United States Patent [19]

Demers et al.

[11] Patent Number: 5,643,950

[45] Date of Patent: Jul. 1, 1997

[54] TRIPHENYLALKYL ANTIMICROBIAL AGENTS

[75] Inventors: James P. Demers, New York, N.Y.; Sigmond Johnson, Three Bridges, N.J.; Michele Ann Weidner-Wells, Somerville, N.J.; Ramesh M. Kanojia, Somerville, N.J.; Stephanie A. Fraga, Somerville, N.J.; Dieter Klaubert, Eugene, Oreg.

[73] Assignee: Ortho Pharmaceutical Corporation, Raritan, N.J.

[21] Appl. No.: 459,446

[22] Filed: Jun. 2, 1995

[51] Int. Cl.$^6$ .......... A61K 31/14; C07C 279/06; C07C 279/08; C07C 211/03
[52] U.S. Cl. .......... 514/539; 514/617; 514/634; 514/643; 514/648; 560/34; 560/37; 564/181; 564/237; 564/316; 564/323; 564/324; 564/330
[58] Field of Search .......... 564/237, 316, 564/323, 324, 330, 181; 514/634, 617, 539, 643, 648; 560/34, 37

[56] References Cited

PUBLICATIONS

M. J. Mahan, J. M. Slauch and J. J. Mekalanos, Science, 259, 686–688 (1993).

S. Roychoudhury et al., Proc. Nat. Acad. Sci., 90, 965–969 (1993) Inhibitors of Two–Component Signal Transduction Systems: Inhibition of Alginate Gene Activation in *Pseudomonas aeruginosa*.

*Primary Examiner*—Alan L. Rotman

[57] ABSTRACT

The invention relates to triphenylalkyl antibacterial compounds of the general formula:

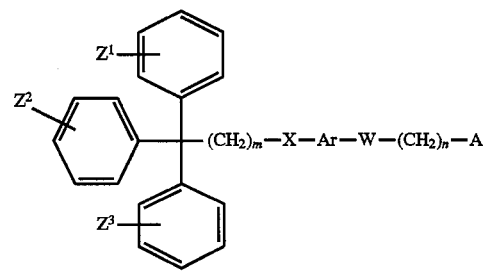

pharmaceutical compositions containing the compounds, and methods for their production and use. These compounds are effective in inhibiting the action of a bacterial histidine protein kinase and are thus useful as anti-infective agents against a variety of bacterial organisms, including organisms which are resistant to other known antibiotics.

16 Claims, No Drawings

TRIPHENYLALKYL ANTIMICROBIAL AGENTS

FIELD OF THE INVENTION

The invention relates to triphenylalkyl antibacterial compounds, pharmaceutical compositions containing the compounds, and methods for their production and use. These compounds are effective in inhibiting the action of a bacterial histidine protein kinase and are thus useful as anti-infective agents against a variety of bacterial organisms, including organisms which are resistant to other known antibiotics.

BACKGROUND OF THE INVENTION

Prokaryotes regulate the transcription of many of their genes in response to changes in the organisms' environment (J. B. Stock, A. M. Stock, and J. M. Mottonen, *Nature*, 344, 395–400 (1990)). Such regulation is essential if the organism is to adapt itself to survival in a changing environment, and pathogenic bacteria rely on such regulatory systems to enable them to survive within their host's body (J. F. Miller, J. J. Mekalanos, S. Falkow, *Science*, 243, 1059 (1989)). Chemical compounds that interfere with the regulatory mechanisms would be expected to be useful anti-infective drugs, as they would prevent bacteria from making necessary adaptive changes in their patterns of gene expression.

Virulence, chemotaxis, toxin production, sporulation, and reproduction are examples of the bacterial processes that are under regulatory control, and which could be inhibited by such compounds. The inhibition of one or more of these processes is expected to lead to reduced virulence, a slowing or halting of bacterial growth and reproduction, and even to bacterial cell death if vital functions are interrupted.

For example, it has been shown that Salmonella species express certain proteins, under regulatory control and in response to the presence of intestinal epithelial cells, which enable them to adhere to and invade these cells. Bacteria unable to synthesize these proteins are avirulent: they cannot cause infection in mice (B. B. Finlay, F. Heffron, S. Falkow, *Science*, 243, 940–943 (1989)). A similar effect would be expected if the genes coding for these proteins were intact, but remained unexpressed.

To accomplish adaptive responses to the environment, bacteria rely on phosphorelay mechanisms, referred to in the art as "two-component switches." These switches have the net effect of transmitting information from the environment to the cell nucleus, where the information is responded to by the switching on or off of transcription of relevant genes. The first step of this phosphorelay scheme relies on numerous histidine protein kinase (HPK) enzymes. Most of these HPK enzymes are sensor molecules, and respond to stimulation by specific environmental signals by transferring phosphate from ATP to a histidine residue of the HPK protein. Some HPK enzymes are stimulated by the presence of acceptor proteins (described below), the concentration of which are modulated by environmental signals. In either case, this auto-phosphorylation is followed by transfer of the phosphate to an aspartyl residue of one or more acceptor proteins (the second components of the two-component switch), which are either regulators of gene expression (by binding to control regions on DNA, or to the RNA polymerase complex) or are themselves kinases for other acceptor molecules. These secondary acceptors may again be regulatory proteins, or kinases toward yet another protein. This cascade of phosphate from protein to protein eventually results in the phosphorylation of one or more regulatory proteins, which then control gene expression.

Mammalian cells do not, or at least are not presently known to, utilize HPK-driven phosphorelay systems for gene regulation. Thus, compounds which selectively inhibit either the autophosphorylation of the HPK protein, or the phosphotransfer step(s), or both, would not be expected to have undesirable effects on the host organism, and are promising candidates for antiinfective drugs. The emergence of drug-resistant pathogenic organisms that are resistant to one or more of the currently available drugs has created a need for novel antibiotics, that act by mechanisms unrelated to those of currently available agents, and inhibitors of HPK would fill this need. The presence of multiple HPK-driven systems (over fifty are currently known) in bacteria gives HPK inhibitors a potential advantage over current antibiotics, in that mutations of a single HPK enzyme are unlikely to confer drug resistance to an organism.

Recently, workers in this field reported a method for detecting bacterial "virulence" genes that are selectively expressed when bacteria infect a host (M. J. Mahan, J. M. Slauch, and J. J. Mekalanos, *Science*, 259, 686–688 (1993)). The potential use of this information in the design of new antibiotics was mentioned, but actual methods of reducing expression of these genes were not described. A preliminary report from another group of workers disclosed inhibitors of the two-component switch controlling alginate gene activation in *Pseudomonas aeruginosa* in an in vitro system (S. Roychoudhury et al., *Proc. Nat. Acad. Sci.*, 90, 965–969 (1993)), but no anti-bacterial activity of the compounds was reported.

SUMMARY OF THE INVENTION

The invention comprises compounds of the general structure 1 shown below:

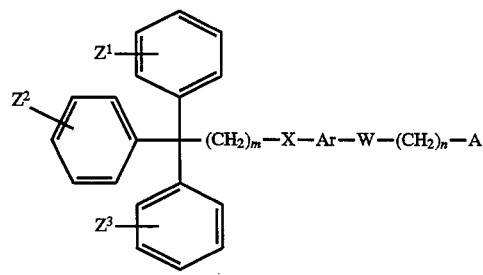

wherein $Z^1$, $Z^2$, and $Z^3$ are independently H, halogen, $C_1$–$C_6$ alkyl, $C_1$–$C_6$ alkoxy, hydroxy, amino, or nitro;

m is an integer from 1–5;

X is $CH_2O$, $CH_2S$, $CH_2NR$, $C(O)NR$, $CH_2OC(O)CH_2$, or $CH_2OC(O)CH_2CH_2$;

Ar is aryl optionally substituted with one to three substituents selected from halogen, hydroxy, $C_1$–$C_6$ alkyl and $C_1$–$C_6$ alkoxy;

W is oxygen, sulfur, or a bond;

n is an integer from 0–5;

A is:
- (a) $NR^1R^2$;
- (b) $N^+R^1R^2R^3$ $B^-$;
- (c) guanidino
- (d) $CO_2H$;
- (e) $CH(R^4)CO_2H$;
- (f) $CH=CHR^5$;
- (g) $CH=C(CO_2H)_2$;
- (h) 5-tetrazolyl;

(i) a moiety of the formula:

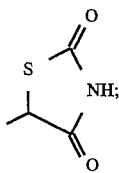

(j) heterocycle optionally substituted with 1–3 substituents selected from $C_1$–$C_6$ alkyl, and aryl-$C_1$–$C_6$ alkyl;

R, $R^1$ $R^2$, and $R^3$ are independently H, $C_1$–$C_6$ lower alkyl, or aryl-$C_1$–$C_6$ alkyl;

$R^4$ is hydrogen or hydroxy;

$R^5$ is:
 (a) $CO_2H$; or
 (b) $C(O)NH(CH_2)_pOH$, wherein p is an integer from 1–4;

$B^-$ is a pharmaceutically acceptable counterion;
wherein aryl is phenyl, biphenyl or naphthyl;
wherein heterocycle is a saturated or unsaturated, charged or uncharged 5 or 6 membered monocyclic ring which has 1, 2, or 3 oxygen, nitrogen or sulfur atoms;
with the provisos that:
 where n is 0, A may also be hydroxy;
 where X is C(O)NH, A is not $CO_2H$; and
 where n is 0, A is not $NH_2$;
 where n is 0 or 1, and W is O or S, A is not OH, $NR^1R^2$, $N^+R^1R^2R^3$ $B^-$ or guanidino;
and the pharmaceutically acceptable salts and prodrug forms thereof.

Another aspect of the invention comprises a method of treating bacterial infections in mammals by administering to a mammal suffering from such infection a therapeutically effective amount of a compound effective in inhibiting the action of a bacterial histidine protein kinase. More particularly, the invention involves a method of treating bacterial infections by inhibiting the autophosphorylation of bacterial histidine protein kinase A or inhibiting the transfer of phosphate from phosphorylated histidine kinases to the aspartyl residue of phosphate acceptor proteins involved in regulation of bacterial gene expression, particularly the operon protein SpoOF.

The compounds of the present invention inhibit the autophosphorylation of bacterial histidine kinases; they also inhibit the transfer of phosphate from phosphorylated histidine kinases to the aspartyl residues of the phosphate acceptor proteins involved in regulation of bacterial gene expression. The compounds of the present invention have been found to inhibit the growth of bacteria by the standard method, measurement of minimum inhibitory concentrations (MIC values). The compounds are useful as bacteriostatic and bactericidal agents, and as anti-infective agents in the treatment of infectious diseases. They may also have utility in increasing the sensitivity of bacteria to conventional antibiotics.

Preferred embodiments of the invention are the compounds where X is $CH_2O$ or $CH_2S$, Ar is phenylene, and where A carries a charge at physiological pH. More preferred are the embodiments where A is amino, guanidino, or comprises a quaternary nitrogen.

DETAILED DESCRIPTION OF THE INVENTION

Relative to the above generic description, certain compounds of Formula I are preferred.

Preferred groups for X are $CH_2O$ and $CH_2S$.

Preferred groups for Ar are 1,2-phenylene, 1,3-phenylene, 1,4-phenylene, 1,6-naphthylene, 6,1-naphthylene, 1,5-naphthylene, 2,5-naphthylene, 5,2-naphthylene, or 2,6-naphthylene.

Preferred groups for A are $NR^1R^2$, guanidino, $CO_2H$, 5-tetrazolyl, $CH=CHCO_2H$, $CH=CHC(O)NHCH_2CH_2OH$, $CH(OH)CO_2H$, $CH=C(CO_2H)_2$, $N^+R^1R^2R^3$ $B^-$, and moieties of the formulae:

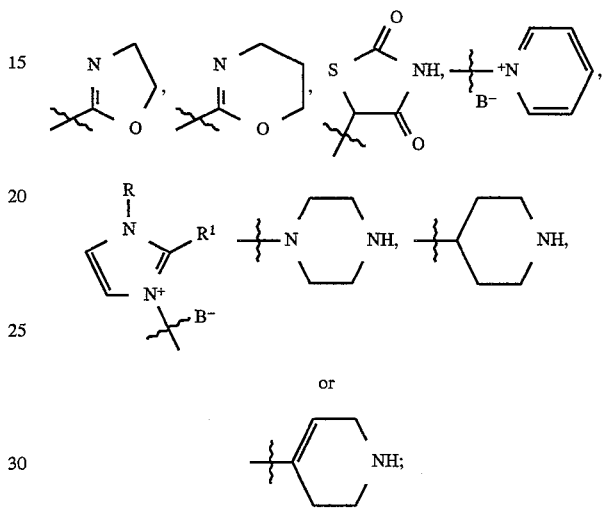

particularly those which carry a charge at physiological pH.

Most preferred of the compounds of Formula I are those in which:

X is selected from $CH_2O$, and $CH_2S$;

Ar is selected from 1,2-phenylene, 1,3-phenylene, or 1,4-phenylene;

Ar may optionally be further substituted with one to three substituents selected from halogen, $C_1$–$C_6$ alkyl, hydroxy, or $C_1$–$C_6$ alkoxy;

n is 1, 2, or 3;

m is 1 or 2;

W is O or a bond; and

A is selected from $NR^1R^2$, guanidino, and $N^+R^1R^2R^3$ $B^-$ wherein $R^1$, $R^2$, and $R^3$ are independently selected from H, $C_1$–$C_6$ lower alkyl, or aryl-$C_1$–$C_6$ alkyl, and wherein $B^-$ is a pharmaceutically acceptable anion.

The compounds of the present invention are prepared in accordance with the methods described below and illustrated in the following Schemes. The key step in the synthetic sequence, when X is $CH_2O$ or $CH_2S$, is shown in Scheme 1, and is usually a Mitsunobu reaction between the appropriately substituted triarylalkanol (2, L=OH) and the appropriately substituted aryl compound 3, wherein B is is the moiety A, a protected A moiety or a precursor for A as described below and in Scheme 2. An alternative to the Mitsunobu method is the reaction of 2, wherein L is halide, sulfonate, or another appropriate leaving group, with the aryl compound 3 in the presence of a suitable base, such as sodium hydride, sodium hydroxide, or potassium carbonate.

Scheme 1

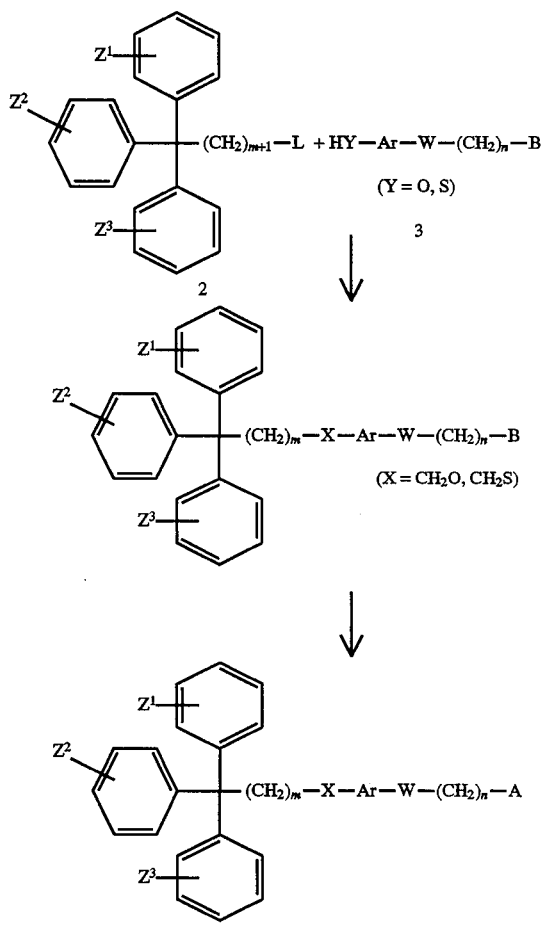

The Mitsunobu reaction may be one of several variants known in the art; the selection of the appropriate phosphine, azodicarbonyl reagent, and solvent will be at the discretion of the practitioner, based on published precedents and on empirical results with the particular combination of substrates to be coupled. Guidance can be found in the review article by D. L. Hughes, in *Organic Reactions*, 42, 335–656 (1992), and in the detailed examples below. In most cases triphenylphosphine ($Ph_3P$) and diethylazodicarboxylate (DEAD), or alternatively tributylphosphine ($Bu_3P$) and (azodicarbonyl)dipiperidine (ADDP), will suffice. Alternatively, displacement of a halide or other leaving group by the appropriate phenoxide or thiophenoxide can be used to generate the $CH_2O$ or $CH_2S$ linkers.

At the time of the Mitsunobu reaction, the group A will in most cases have to be in a protected form B, or else (for instance when A is a heterocyle) B will be a precursor functional group convertible into the desired heterocycle or other group A. Once the linker X has been established, the group B is converted, if necessary, into the desired group A, as shown in Scheme 2. Suitable protecting groups for guanidines and amines include, but are not limited to, trifluoroacetyl, t-butoxycarbonyl (Boc), and benzyloxycarbonyl. The case where Ar is 1,4-phenylene is shown in Scheme 2 for purposes of illustration only; the chemical processes presented in the scheme are in general applicable to all definitions of Ar.

Suitable protecting groups for carboxylic acids include, but are not limited to, lower alkyl esters or benzyl esters; suitable precursor groups include olefin, nitrile, or oxazolidine. For cases where B=NHBoc, NHC(=NBoc)NHBoc, $CO_2R$, or $CH=CHCO_2R$, the intermediates are deprotected after the Mitsunobu reaction to afford amines, guanidines or carboxylic acids, respectively. For cases where B=CN, the nitrile may be hydrolyzed to a carboxylic acid, reduced to provide an amine, or converted to a tetrazole; where B=an olefin, it may be oxidized with ozone or other reagents to provide an aidehyde or acid. Where B=CHO, NHBoc, $CO_2R$, or $CH=CHCO_2R$, the compounds may be converted into those of structure 1 where A is one of the heterocycles described. In the cases where A is a piperidine or piperazine, the terminal nitrogen is protected during the Mitsunobu reaction in the manner described above for amines.

Scheme 2

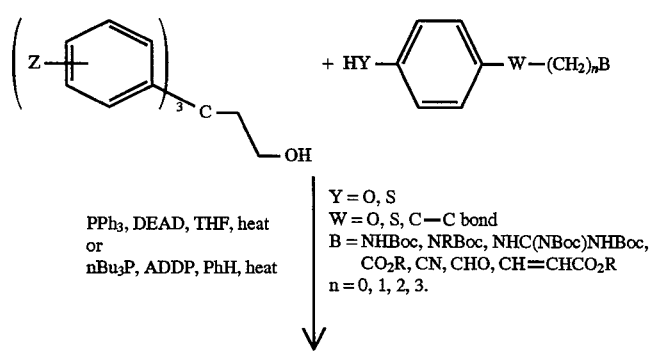

PPh3, DEAD, THF, heat
or
nBu3P, ADDP, PhH, heat

Y = O, S
W = O, S, C—C bond
B = NHBoc, NRBoc, NHC(NBoc)NHBoc,
    $CO_2R$, CN, CHO, $CH=CHCO_2R$
n = 0, 1, 2, 3.

-continued
Scheme 2
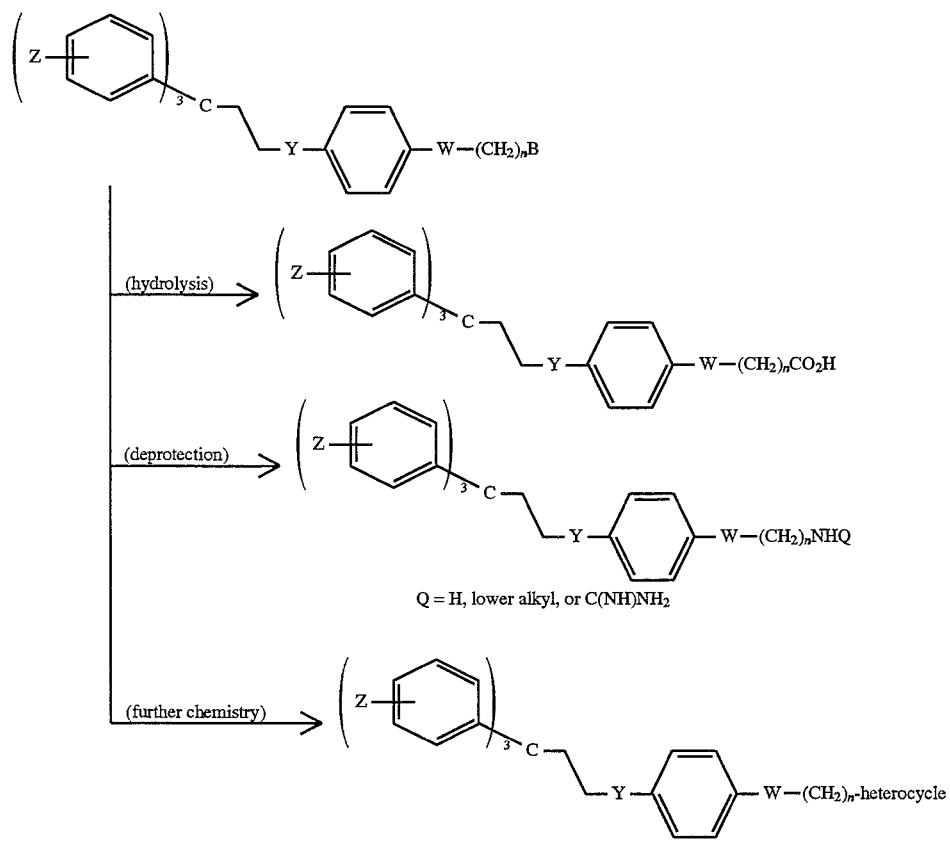
Q = H, lower alkyl, or C(NH)NH$_2$
Scheme 3
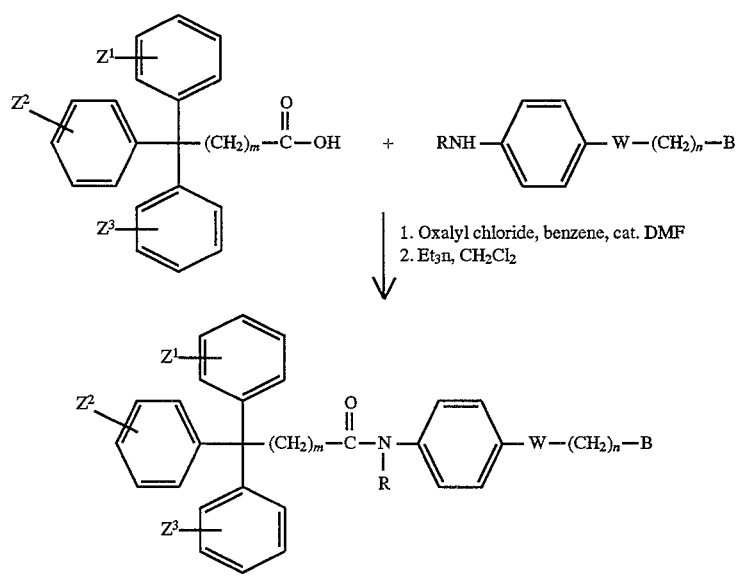
1. Oxalyl chloride, benzene, cat. DMF
2. Et$_3$n, CH$_2$Cl$_2$ Scheme 4

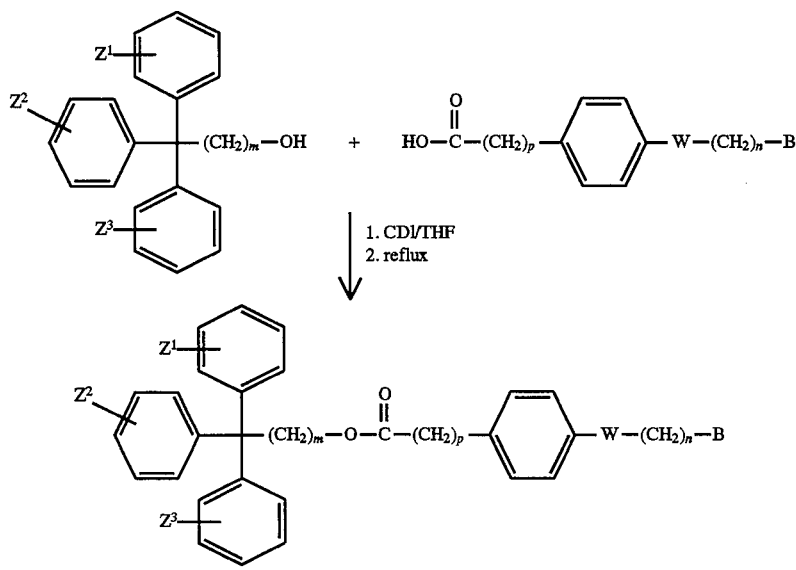

Where B=CHO, reduction to the corresponding alcohol and subsequent conversion to the chloride (1, A=Cl) followed by reaction with a nitrogen-containing heterocycle, permits preparation of quaternary heterocyclic values of A, such as the pyridinium and imidazolium derivatives exemplified below. The chloride can also be used to quaternize tertiary aliphatic amines, giving 1 where A=N$^+$R$^1$R$^2$R$^3$, or may be reacted with primary or secondary amines to give cases where A=NR$^1$R$^2$. Compounds where B=CHO are also useful precursors to acids via oxidation, to alcohols via reduction, to the phenol (if n=0 and W is a bond) by Baeyer-Villiger oxidation, and to alpha-hydroxy acids (A=CH(OH)COOH) via addition of trihalomethyl anions. Specific examples of these processes are to be found below.

In cases where X=C(O)NR or CH$_2$OC(O)(CH$_2$)$_p$, a coupling reaction to generate the linker X is performed with the appropriately substituted acid and the appropriately substituted aniline or alcohol derivative. In Schemes 3 and 4, examples where Ar is 1,4-phenylene are illustrated, but the methods are applicable to any definition of Ar. As with the Mitsunobu reaction, it will sometimes be necessary that group B is a precursor or protected form of group A, as defined as in Scheme 2, and is subsequently converted into the desired group A as in Scheme 2. In general, the carboxylic acid partner of the coupling reaction is activated with one of a variety of reagents, such as carbonyldiimidazole (CDI), thionyl chloride, oxalyl chloride, or a carbodiimide reagent such as dicyclohexylcarbodiimide (DCC). The coupling reactions may be chosen from, but are not limited to, the ones illustrated in the scheme and described further below. There are a wide variety of coupling methods known to one skilled in the art, and the majority of them would be applicable to the reactions in Schemes 3 and 4.

The starting materials for the Mitsunobu and acylation coupling reactions of Schemes 3 and 4 are, in general, known classes of compounds, and are prepared by routine methods, illustrated in Schemes 5 and 6. In Scheme 5, the triarylalkanoic acid and triarymethane starting materials are in some cases commercially available, others can be prepared by various published methods (J. W. Wilt, J. A. Lundquist, *J. Org. Chem.*, 29, 921 (1964); W. H. Starnes Jr., *J. Org. Chem.*, 3:3, 2767 (1968). The conversion of the acids to triarylalkanols by borane reduction is a known synthesis (M. Said et al., *Biochem. Biophys. Res. Comm.*, 187, 140–145 (1992)), modified in the present case by the addition of trimethyl borate to accelerate the reaction. The chain-extension of a triarylalkanol to the next-higher triarylalkanoic acid then makes the next higher value of m accessible (McPhee, Lindstrom, *J. Amer. Chem. Soc.*, 65, 2177 (1943). The triarylalkanols may also be prepared from the corresponding triarylmethanes as shown (C. G. Screttas, M. Micha-Screttas, *J. Org. Chem.*, 47, 3008–3011 (1982), also H. W. Gibson et al., *J. Org. Chem.*, 58, 3748–3756 (1993)). The various groups Z are compatible with one or more of these synthetic approaches. Alternatively, the triarylalkanoic acid can be prepared and then nitrated, and the resulting isomers separated by chromatography. The nitro groups can be reduced to amino, and then via diazotization to halogen, hydroxy, or alkoxy groups.

In Scheme 6, reaction of 2-(4-hydroxyphenyl)ethylamine with di-t-butyldicarbonate, to afford a protected phenolic coupling component for the Mitsunobu reaction, is illustrated. A variety of (hydroxyphenyl)alkylamines and (hydroxyphenoxy)alkylamines are commercially available or are known compounds; they can be synthesized by common methods such as reductive amination of benzaldehydes, hydrogenation of arylacetonitriles or aryloxyacetonitriles, reduction of cinnamides or cinnamylamines, etc. Methods for their preparation can be chosen from, but are not limited to, the examples presented herein. Where X is to be CH$_2$S, 4-mercaptobenzaldehyde may be coupled via the Mitsunobu reaction to the desired triarylalkanol, and the aidehyde then converted to the desired group (CH$_2$)$_n$—A or (CH$_2$)$_n$—B by the methods discussed below.

Also in Scheme 6, the generation of a protected guanidine from the corresponding amine is illustrated, again providing a phenolic component for the Mitsunobu coupling. The illustrated use of N,N'-bis(t-butoxycarbonyl)-S-methylisothiourea for this purpose is a known procedure (R. J. Bergeron, J. S. McManis, *J. Org. Chem.*, 52, 1700–1703 (1987), it is in some cases improved by the addition of silver acetate to the reaction mixture. (See also M. S. Bernatowicz, Y. Wu, G. R. Matsueda, *Tetrahedron Letters*, 34, 3389

(1993)). These methods are in general applicable to all amines with the various definitions of Ar, X, W, and n.

Alternatively, one can prepare 1 with A=$NH_2$ and then convert the amino group into a guanidino group by the above or by other known methods (e.g., M. S. Bernatowicz, Y. Wu, G. R. Matsueda, *J. Org. Chem.*, 57, 2497–2502 (1992) and references therein).

n=0 by oxidation (B. O. Lindgren, T. Nilsson, *Acta Chem. Scand.*, 27, 888 (1973)), where n=1 by chain extension (K. Shaw, M. Armstrong, A. McMillan, *J. Org. Chem.*, 21, 1149 (1956)), where n=2 by condensation with malonic acid to give the cinnamic acid (J. Koo et al., *Org. Syn. coll. vol.* IV, 327 (1963)), followed by hydrogenation if desired, and where n=3 by homologation with a phosphorous ylide (J. G.

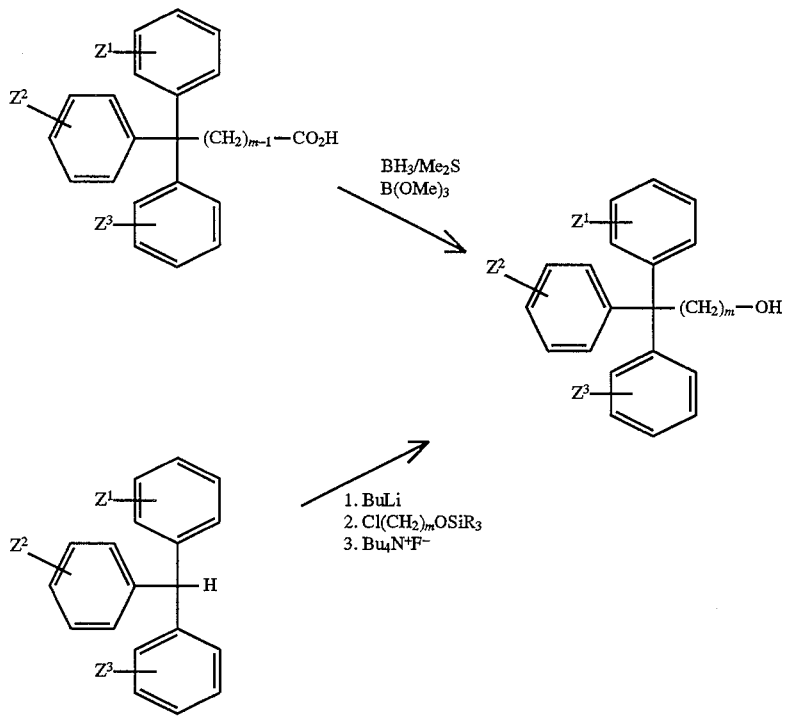

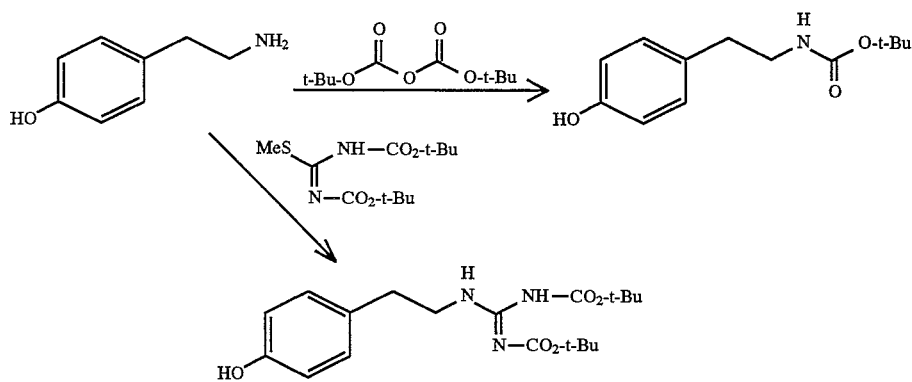

Scheme 7 illustrates the preparation of compounds where A=$CO_2H$, and conversion of these to N-(hydroxyalkyl) amides, followed by cyclization to give the claimed oxazolidine or dihydro-oxazine derivatives. The starting omega-(hydroxyphenyl)alkanoic esters (or the corresponding acids) in Scheme 7 are known compounds; novel examples with further substitution on the ring can be prepared as described further below, or by other methods known to the art. For example, beginning with optionally substituted 4-hydroxy or 4-methoxy benzaldehydes, one can obtain the case where Cannon et al., *J. Med. Chem.*, 32, 2210 (1989)), again followed by hydrogenation if desired. As shown in Scheme 8, these reactions can also be performed on 1 where A=CHO, giving the corresponding acids directly; these methods are also applicable to the other disclosed definitions of Ar.

Where n is 0 and A is CHO, one may perform a Baeyer-Villiger oxidation on 1 to obtain the phenol wherein n is 0 and A is OH, and then O-alkylate this phenol via appropriate Mitsunobu or nucleophilic displacement reactions as described above to attach the group $(CH_2)_nA$ or $(CH_2)_nB$, thereby obtaining the cases where W is oxygen. Alternatively, one can submit the known compounds 2-(phenylsulfonyloxy)phenol or 3-(phenylsulfonyloxy)phenol to the reactions of Scheme 1, and then remove the phenylsulfonyl group by hydrolysis. Examples of both approaches to the cases where W is oxygen are provided below.

Where it is desired that W be sulfur, a suitable precursor group is nitro. For example, one would submit 4-nitrophenol to the Mitsunobu reaction of Scheme 1, generating an intermediate where n=0 and B is a nitro group. Reduction, diazotization and reaction with a xanthate (the Leuckart thiophenol synthesis, see D. S. Tarbel, *J. Amer. Chem. Soc.*, 74, 48 (1952)), provides the thiophenol, and alkylation with an alkylating agent such as $Br(CH_2)_nA$ or $Br(CH_2)_nB$ then provides access to the desired material.

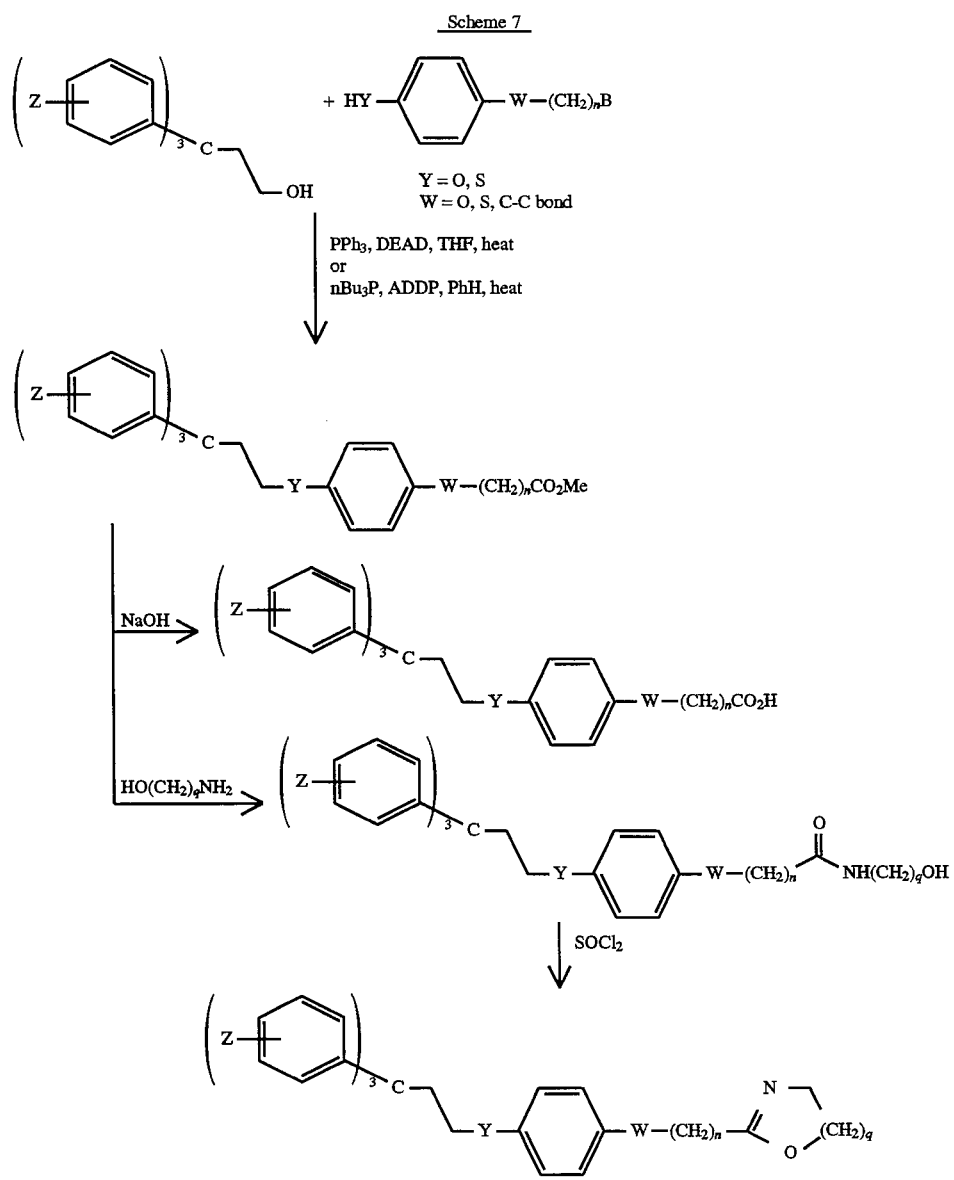

Scheme 7

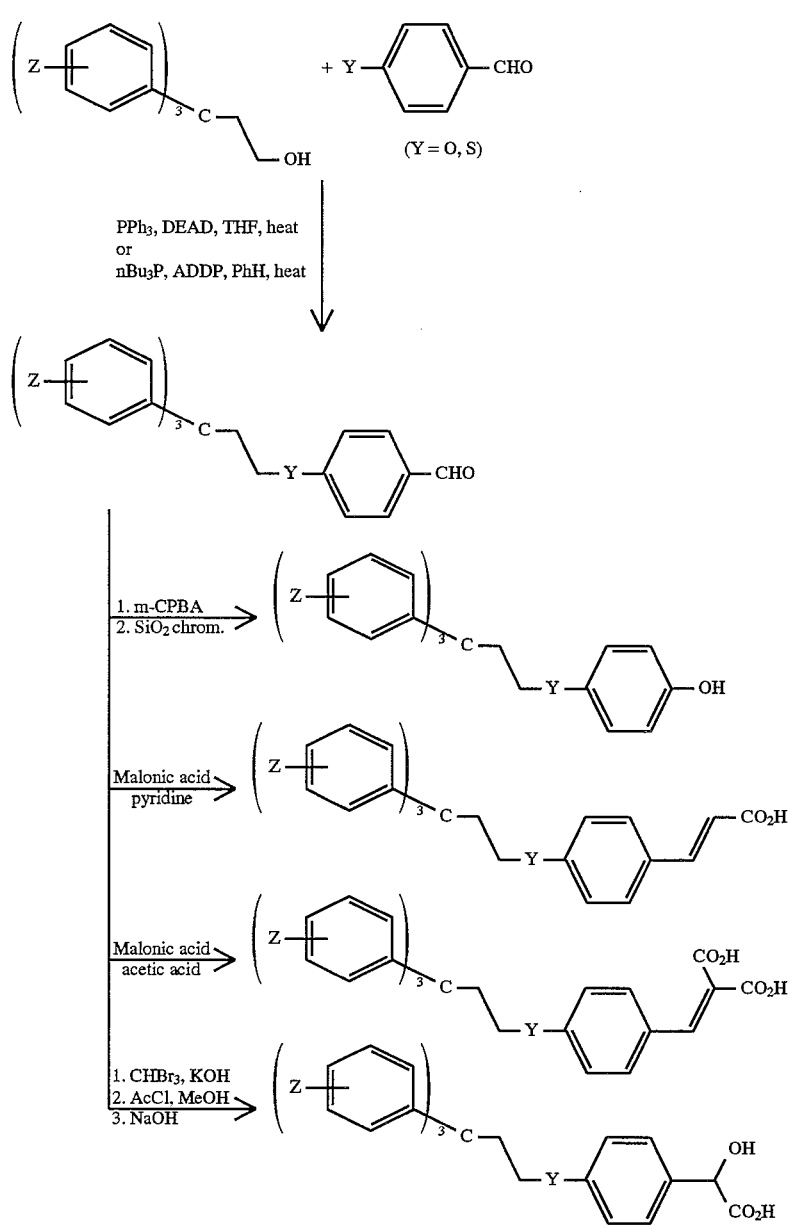

Scheme 8

The foregoing reactions are performed in a solvent appropriate to the reagents and materials employed and suitable for the transformation being effected. It is understood by those skilled in the art of organic synthesis that the various functionalities present on the molecule must be consistent with the chemical transformations proposed. This will frequently necessitate judgment as to the order of synthetic steps, protection of reactive groups, and selection of reaction conditions. Reaction conditions compatible with the substituents employed will be apparent to one skilled in the art, as will be the selection of protecting groups where needed.

From formula 1 it is evident that some of the compounds of the invention may have one or more asymmetrical carbon atoms in their structure. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diasteromeric salts with optically active acids or bases or by chiral chromatography. Pure stereoisomers may also be prepared synthetically from appropriate stereochemically pure starting materials, or by using stereospecific reactions.

Suitable pharmaceutical salts are those of inorganic or organic acids, such as hydrochloric acid, hydrobromic acid, hydroiodic acid, sulfuric acid, nitric acid, phosphoric acid, acetic acid, succinic acid, oxalic acid, malic acid and the like. Suitable salts are also those of inorganic or organic bases, such as KOH, NaOH, $Ca(OH)_2$, $Al(OH)_3$, piperidine, morpholine, ethylamine, triethylamine and the like.

Also included within the scope of the invention are the hydrated forms of the compounds which contain various amounts of water, for instance, the hydrate, hemihydrate and sesquihydrate forms.

The ability of bacteria to quickly respond to changes in the environment is of utmost importance for their survival. Bacteria are capable of rapidly responding and adapting to such diverse stimuli as changes in nutrients, osmolarity, temperature, light, or host environment. These responses may be transient, such as those required for changes in motility or for entry into a host cell. Alternatively, the responses may require major shifts in gene expression and cell morphology, such as those required for sporulation, or for survival within a macrophage. The mechanism by which bacteria are able to sense cues from the physical environment (or from within the cytoplasm) and process these signals into appropriate responses often involves the so-called "two-component" systems.

As stated above, the treatment method of the present invention is based on the inhibition of this "two-component switch" system. All bacteria use this mechanism to control various adaptive/virulence factors to facilitate establishment of a bacterial population in the environment (for example, a bacterial infection in a host). The system invariably consists of a sensor which either activates a kinase or is a part of the kinase, and which upon stimulation, autophosphorylates. This phosphorylated species is a highly active phosphodonor which immediately transfers its phosphate to a "regulatory" component, which in turn initiates the biological response such as transcription or further phosphotransfer in a cascade which eventually ends in regulation of bacterial gene expression. Although each of the kinases and response regulators has a unique sequence (in fact, even functionally identical proteins have slightly different sequences in different species) they share a homologous biochemical mechanism and they share significant homology in the active site.

As stated, the present invention provides compounds which exhibit antibiotic activity by inhibiting the autophosphorylation of bacterial histidine kinases. They also inhibit the transfer of phosphate from phosphorylated histidine kinases to the aspartyl residues of the phosphate acceptor proteins involved in regulation of bacterial gene expression.

This invention further provides a method of treating bacterial infections, or enhancing the activity of other antibacterial agents, in warm-blooded animals, which comprises administering to the animals a compound of the invention alone or in admixture with a diluent or in the form of a medicament according to the invention.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacological acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, preferably given in divided doses two to four times a day, or in sustained release form. For most large mammals the total daily dosage is from about 0.07 g to 7.0 g, preferably from about 100 mg to 1000 mg Dosage forms suitable for internal use comprise from about 100 mg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

The compounds of the present invention have antibacterial activity as determined by the following tests. First, the compounds were tested for their activity in inhibiting the autophosphorylation of Kinase A and the transphosphorylation of SpoOF, two proteins involved in one of the above described signal transduction systems controlling gene expression in bacteria. Representative compounds were then tested for antibacterial activity against selected organisms by the standard MIC method. The results are set forth below.

Table 1 lists examples of compounds of the invention, along with their $IC_{50}$ values in the HPK in vitro assay described below, and MIC value ranges for the selected microorganisms identified below. These examples are merely illustrative of the invention, and are not intended to limit the scope of the claims in any way. In the table, the first locant of each Ar group is the carbon bearing the substituent —X—; the second locant refers to the carbon bearing the substituent —W—.

TABLE 1

| Ex. # | $Z^1,Z^2,Z^3$ | m | X | Ar | W | n | A | $IC_{50}$ (μM) | MIC (μg/mL) |
|---|---|---|---|---|---|---|---|---|---|
| 1 | H,H,H | 1 | CONH | 1,4-phenylene | — | 0 | 1-piperazinyl | 200 | |
| 2 | H,H,H | 1 | $CH_2O$ | 1,4-phenylene | — | 0 | 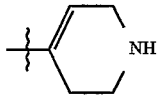 | 170 | |
| 3 | H,H,H | 1 | $CH_2O$ | 1,4-phenylene | — | 2 | $NH_2$ | 14 | 2–4 |
| 4 | H,H,H | 1 | $CH_2O$ | 1,4-phenylene | — | 1 | $NH_2$ | 19 | |
| 5 | H,H,H | 1 | $CH_2O$ | 1,4-phenylene | — | 2 | $NH(=NH)NH_2$ | 5 | 1–2 |
| 6 | Cl,Cl,Cl | 1 | $CH_2O$ | 1,4-phenylene | — | 2 | NH2 | 150 | |
| 7 | H,H,H | 1 | $CH_2O$ | 1,3-phenylene | — | 2 | NH2 | 80 | |
| 8 | H,H,H | 1 | $CH_2O$ | 6-OMe-1,3-phenylene | — | 2 | NH2 | 27 | 4 |
| 9 | Cl,Cl,Cl | 1 | $CH_2O$ | 1,4-phenylene | — | 2 | $NH(=NH)NH_2$ | 21 | 8 |
| 10 | H,H,H | 3 | $CH_2O$ | 1,4-phenylene | — | 2 | $NH(=NH)NH_2$ | 15 | 2–4 |
| 11 | H,H,H | 2 | $CH_2O$ | 1,4-phenylene | — | 2 | $NH(=NH)NH_2$ | 21 | |
| 12 | H,H,H | 1 | $CH_2O$ | 1,4-phenylene | — | 2 | COOH | 51 | 2–16 |
| 13 | H,H,H | 1 | $CH_2O$ | 1,4-phenylene | — | 1 | COOH | 50 | 8–16 |
| 14 | H,H,H | 1 | $CH_2S$ | 1,4-phenylene | — | 2 | COOH | 34 | 4–8 |
| 15 | H,H,H | 1 | $CH_2O$ | 1,4-phenylene | — | 3 | COOH | 14 | 8–64 |
| 16 | H,H,H | 1 | CONH | 1,4-phenylene | — | 2 | NH2 | 59 | 32–64 |
| 17 | H,H,H | 1 | $CH_2O$ | 2,6-naphthylene | — | 0 | COOH | 300 | 4–64 |
| 18 | H,H,H | 1 | CONH | 1,4-phenylene | — | 2 | $NH(=NH)NH_2$ | 51 | 4–16 |
| 19 | H,H,H | 1 | $CH_2O$ | 1,4-phenylene | — | 2 | 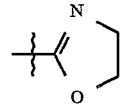 | 260 | |
| 20 | H,H,H | 1 | $CH_2O$ | 2,6-naphthylene | — | 1 | NH2 | 75 | 4–8 |
| 21 | H,H,H | 1 | $CH_2O$ | 1,4-phenylene | — | 0 | COOH | 290 | 8->128 |
| 22 | H,H,H | 1 | $CH_2O$ | 1,4-phenylene | — | 0 | t-CH=CHCOOH | 71 | 4–64 |
| 23 | H,H,H | 1 | $OC(O)CH_2$ | 1,4-phenylene | — | 0 | OH | 170 | >128 |
| 24 | H,H,H | 1 | $OC(O)(CH_2)_2$ | 1,4-phenylene | — | 0 | OH | 160 | >128 |
| 25 | H,H,H | 1 | $CH_2O$ | 1,4-phenylene | — | 0 | 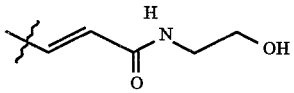 | 150 | >128 |
| 26 | H,H,H | 1 | $CH_2O$ | 1,4-phenylene | — | 2 | 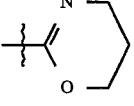 | 43 | 8–16 |
| 27 | H,H,H | 1 | $CH_2O$ | 1,4-phenylene | — | 2 | 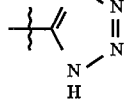 | 11 | 8–64 |
| 28 | H,H,H | 1 | $CH_2O$ | 1,4-phenylene | — | 1 | $N^+(Me)_2CH_2Ph$ | 13 | 2 |
| 29 | H,H,H | 1 | $CH_2O$ | 1,4-phenylene | — | 1 | 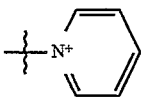 | 6 | 2–4 |

TABLE 1-continued

| Ex. # | $Z^1, Z^2, Z^3$ | m | X | Ar | W | n | A | $IC_{50}$ (μM) | MIC (μg/mL) |
|---|---|---|---|---|---|---|---|---|---|
| 30 | H,H,H | 1 | $CH_2O$ | 1,4-phenylene | — | 1 | 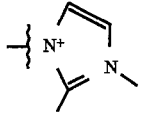 | 28 | 2–8 |
| 31 | H,H,H | 1 | $CH_2O$ | 1,4-phenylene | — | 0 | $CH=C(COOH)_2$ | 54 | >128 |
| 32 | H,H,H | 1 | $CH_2O$ | 1,4-phenylene | — | 1 | 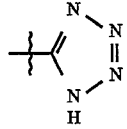 | 19 | 8–64 |
| 33 | H,H,H | 1 | $CH_2O$ | 1,4-phenylene | — | 1 | $N^+(Me)_3$ | 29 | 4–8 |
| 34 | H,H,H | 1 | $CH_2O$ | 1,3-phenylene | — | 1 | COOH | 38 | 32 |
| 35 | H,H,H | 1 | $CH_2O$ | 1,3-phenylene | — | 2 | COOH | 42 | 4–128 |
| 36 | H,H,H | 1 | $CH_2O$ | 1,2-phenylene | — | 1 | COOH | 45 | 16–32 |
| 37 | H,H,H | 1 | $CH_2O$ | 1,4-phenylene | — | 0 | CH(OH)COOH | 73 | 32->128 |
| 38 | H,H,H | 1 | $CH_2O$ | 1,2-phenylene | — | 2 | COOH | 27 | |
| 39 | H,H,H | 1 | $CH_2O$ | 1,4-phenylene | — | 0 | 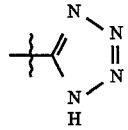 | 110 | |
| 40 | H,H,H | 1 | $CH_2S$ | 1,4-phenylene | — | 3 | NH2 | 13 | |
| 41 | H,H,H | 1 | $CH_2O$ | 1,4-phenylene | — | 0 | 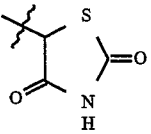 | 18 | |
| 42 | H,H,H | 1 | $CH_2O$ | 3-OH-1,2-phenylene | — | 0 | COOH | 85 | |
| 43 | H,H,H | 1 | $CH_2O$ | 1,3-phenylene | — | 0 | t-CH=CHCOOH | 40 | |
| 44 | H,H,H | 1 | $CH_2O$ | 1,3-phenylene | O | 1 | COOH | 71 | |
| 45 | H,H,H | 1 | $CH_2O$ | 1,2-phenylene | O | 1 | COOH | | |
| 46 | H,H,H | 1 | $CH_2O$ | 1,3-phenylene | O | 3 | COOH | 16 | |
| 47 | H,H,H | 1 | $CH_2O$ | 1,2-phenylene | O | 3 | COOH | | |
| 48 | H,H,H | 1 | $CH_2O$ | 1,4-phenylene | O | 1 | COOH | | |
| 49 | H,H,H | 1 | $CH_2O$ | 1,4-phenylene | O | 3 | COOH | | |

The protocols for the above referenced assays are as follows.

1. Autophosphorylation of Kinase A and Transphosphorylation of SpoOF Assay

To study the effect of the compounds of the present invention on the signal transduction process in bacteria, the inhibiting effect of the compounds on the sporulation operon proteins Kinase A and SpoOF was examined. Specifically, the inhibition of autophosphorylation of Kinase A and the transphosphorylation of SpoOF was determined in the following assays. The SpoOF response regulator is the primary substrate for phosphorylation by the protein kinase, Kin A, involved in the sporulation process in bacteria. See D. Burbulys, K. A. Trach, J. A. Hoch, Cell, 64, 545–552 (1991). SpoOF and KinA were prepared from recombinant E. coli overexpressing the proteins (J. Cavanagh et al, Amino Acids, 6, 131–140 (1994) and references therein).

The following stock reagents were either prepared and used promptly or stored at the indicated temperature:

8 X Salts: 2M KCl (5 mL), 1M $MgCl_2$ (800 mL), 1M $CaCl_2$ (100 mL), 10 mg/mL phenylmethylsulfonyl fluoride (200 mL), 1M dithioreitol (50 mL), 0.25M $Na_2EDTA$ (32 mL) and $H_2O$ 3.82 mL (−20° C.)

5X Loading Dye: 0.5M TRIS-HCl-pH 6.8 (7.5 mL), 10% SDS (2 mL) 0.1% bromophenol blue (0.5 mL), 100% glycerol (3 mL) and 12.5M 2-mercaptoethanol (0.3 mL)

1–1.3 mg/mL KinA: 15 mM TRIS-HCl, pH 8.0, 6 mM KCl; 4 mM 2-mercaptoethanol; 40% glycerol (−20° C.)

1 mg/mL SpoOF: 17.5 mM TRIS-HCl, pH 8.0; 0.7 mM KCl; 0.7 mM $MgCl_2$; 0.7 mM $CaCl_2$; 5mM 2-mercaptoethanol; 30% Glycerol (−20° C.)

5% Stacking Gel: 40% 29:1 acrylamide:bis acrylamide (1.25 mL), 0.5M TRIS-HCl, pH 6.8 (2.5 mL), 10% SDS (0.1 mL), D-$H_2O$ (6.15 mL) 10% ammonium persulfate (100 mL) and TEMED (25 mL) SDS Running Buffer: TRIS-BASE (3.02 g), glycine (14.4 g) SDS (1 g), D-$H_2O$ (to 1 L)

The reaction mixture was prepared from 8X Salts (87 μL), 1M TRIS, pH 8 (118 μL), 50% glycerol (63 μL), SpoOF (14.1 ML) and KinA (7.0 μL). Microcentrifuge tubes were charged with the reaction mixture (18.5 μL) and a 1.0 mM solution of the test compound in 5% DMSO (18.5 μL), and incubated for 15 min on ice. 100 mM ATP solution (3.0 μl, containing 625 μCi [$^{32}$P]ATP) was added, and the mixture left for 10 minutes at room temperature. The reaction was quenched with 5X loading dye (10 µL per tube) and the samples were loaded on a prepared 5% Stacking Gel, or stored on dry ice until ready for use. The prepared wells were filled with SDS Running Buffer, samples were loaded into the wells, and 80 volts were applied to the gel until the dye front reached the bottom of the stacking gel. The voltage was then increased to 250 volts until electrophoresis was complete. Radioactive bands in the gel corresponding to phosphorylated KinA and SpoOF were imaged and quantitated with a phosphoimager.

If either enzyme was inhibited (as evidenced by the absence of labelled protein in the developed gel), an $IC_{50}$ was calculated by running the assay with a range of inhibitor concentrations from 1 to 500 µM. After electrophoresis of the reaction mixtures, percent inhibition was determined by measuring the concentration of radioactive phosphorus with a phosphoimager and calculating the values using a software program (BioRad Molecular Analyst).

2. MIC Anitimicrobial Assay

The in vitro antimicrobial activity of the compounds was determined by the microdilution broth method following the test method from the National Committee for Laboratory Standards (NCCLS). This method is described in the NCCLS Document M7-A2, Vol.10, No.8 "Methods for Dilution Antimicrobial Susceptibility Test for Bacteria that Grow Aerobically—Second Edition."

In this method two-fold serial dilutions of drug in cation supplemented Mueller-Hinton broth are added to wells in microdilution trays. The test organisms are prepared by adjusting the turbidity of actively growing broth cultures so that the final concentration of test organism after it is added to the wells is approximately $5\times10^4$ CFUs/well).

Following inoculation of the microdilution trays, the trays are incubated at 35° for 16–20 hours and then read. The MIC is the lowest concentration of test compound that completely inhibits growth of the test organism. The amount of growth in the wells containing the test compound is compared with the amount of growth in the growth-control wells (no test compound) used in each tray.

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

Methods of preparing the exemplified compounds of the invention are presented below. These examples are intended to illustrate the methods of synthesis, and are not intended to limit the scope of the claims in any way. Abbreviations used: DEAD, diethyl azodicarboxylate; $Ph_3P$, triphenylphosphine; $Bu_3P$, tri-n-butylphosphine; THF, tetrahydrofuran; DMF, N,N-dimethylformamide; ADDP, 1,1'-(azodicarbonyl)dipiperidine.

Reference Example 1. 3,3,3-triphenylpropanol.

Borane-methyl sulfide (60 mL, 0.63 mol) was added dropwise to 100 g (0.33 mol) of 3,3,3-triphenylpropanoic acid and 38 mL (0.33 mol) trimethyl borate in 1 liter of anhydrous tetrahydrofuran at room temperature. After 18 hr, the reaction mixture was carefully acidified with 180 mL of conc. hydrochloric acid, stirred for 3 hours and then further diluted with ca. 450 mL of water. The THF layer was collected, the aqueous layer extracted twice with dichloromethane, and the organic layers combined and dried over magnesium sulfate. The organic solution was evaporated to leave a solid, which was recrystallized (two crops) from hexane-dichloromethane to give 83.3 g (87.5%) of the title compound, mp 103°–106° C.

Reference Example 2. 5,5,5-triphenylpentanol.

t-Butylchlorodimethylsilane (8.3 g, 55 mmol) was added to a stirred mixture of 4-chlorobutanol (5.0 mL, 50 mmol), silver nitrate (12.8 g, 75.1 mmol), and pyridine (4.0 mL, 50 mmol) in 40 mL of dry THF. After 4 hr, the reaction mixture was filtered through Celite and evaporated to give a yellow oil. The material was purified by distillation to provide 4-chlorobutyl t-butyldimethylsilyl ether as a colorless oil (11 g, quantitative). To a solution of triphenylmethane (5.10 g, 20.8 mmol) in 25 mL of dry THF at −78° C., 13.1 mL (21 mmol) of 1.6M n-butyllithium was added dropwise under nitrogen. Shortly thereafter, 4.29 g (19.3 mmol) of 4-chlorobutyl t-butyldimethylsilyl ether was added. After addition of water and extraction with hexane, the product was purified by chromatography on silica gel with 1:3 dichloromethane-hexane, providing t-butyldimethylsilyl 5,5,5-triphenylpentyl ether as an oil (6.85 g). This material was dissolved in THF (30 mL) and 16 mL of 1.0M tetrabutylammonium fluoride in THF was added. After 3 hr, the mixture was acidified with 1N HCl, extracted with three portions of ethyl acetate, and the extracts dried over magnesium sulfate and evaporated in vacuo. The product was purified by chromatography on silica gel with a 10%–20% gradient of ethyl acetate in hexane, providing the title compound as a white solid, 3.83 g (63% overall).

Reference Example 3. N-(t-butoxycarbonyl)-4-hydroxybenzylamine.

Using the method of L. Farber and P. Gradeif, U.S. Pat. No. 4,388,250, 4-hydroxybenzaldehyde was reductively aminated to produce 4-hydroxy benzylamine, obtained as a crystalline monohydrate after dilution of the filtered reaction mixture with water. This material (12 g, 85 mmol) was suspended in THF (150 mL), cooled in an ice bath, and di-t-butyl dicarbonate (19 g, 87 mmol) was added. The mixture was stirred overnight, then concentrated to a viscous oil. Addition of water (250 mL) and vigorous stirring overnight converted the oil into a white powder, mp 8820 −91° C. (21 g).

Reference Example 4. N-(t-butoxycarbonyl)-3-hydroxybenzylamine.

By the procedure above, but beginning with 3-hydroxybenzaldehyde, 3-hydroxybenzylamine was obtained as a tan crystalline solid, mp 168°–171° C. after recrystallization from isopropanol. This was converted as above into the title compound, obtained as a tan powder, mp 79°–81° C. after crystallization from hexane-carbon tetrachloride.

Reference Example 5. N-(t-butoxycarbonyl)-2-(4-hydroxyphenyl)ethylamine.

Tyramine (5.58 g, 40.7 mmol) was dissolved in 50 mL of THF at 5° C. Di-t-butyl dicarbonate (8.90 g, 40.8 mmol) in 25 mL of THF was added dropwise. The reaction was allowed to warm to ambient temperature overnight, then diluted with water, extracted three times with ethyl acetate, and the organic extracts dried over $MgSO_4$ and concentrated in vacuo. The crude brown solid, 8.93 g (93%) was used as is.

Reference Example 6. N-(t-butoxycarbonyl)-2-(3-hydroxyphenyl)ethylamine.

3-Hydroxyphenethylamine hydrochloride (11.5 g, 66.2 mmol) and 1.0N aqueous sodium bicarbonate (1 00 mL) were dissolved in 100 mL of THF and cooled to 5° C. Di-t-butyl dicarbonate (14.5 g, 66.2 mmol) in 100 mL of THF was added dropwise. The reaction was allowed to warm to ambient temperature overnight, then diluted with water, extracted three times with ethyl acetate, and the organic extracts dried over $MgSO_4$ and concentrated in vacuo. The product was recrystallized in two crops from hexane-dichloromethane to provide 13.9 g (88%) of the title compound as a tan solid, mp 79°–82° C.

Reference Example 7. N-(t-butoxycarbonyl)-3-(4-hydroxyphenyl)propylamine.

A mixture of 3-(4-hydroxyphenyl)propionitrile (5.0 g, 34 mmol), 5% rhodium on alumina (0.5 g), methanol (75 mL) and concentrated ammonium hydroxide solution (25 mL) was shaken under 50 psi hydrogen for 40 hr. Filtration and evaporation of solvent left crude 3-(4-hydroxyphenyl) propylamine as a colorless oil. This oil was dissolved in THF (100 mL) and di-t-butyl dicarbonate (8.5 g, 38 mmol) was added. When the ensuing exothermic reaction and gas evolution ceased, the mixture was concentrated to an oil, and chromatographed on silica gel with 1% isopropanol in 5:1 hexane-ethyl acetate. The title compound was obtained as a colorless gum (5.1 g).

Reference Example 8. N,N'-Bis(t-butoxycarbonyl)-N"-(4-hydroxyphenyl)methylguanidine.

4-hydroxybenzylamine hydrate, prepared as above (5.33 g) and N,N'-Bis(tert-butoxycarbonyl)-S-methylisothiourea (10.96 g) were combined in 150 mL THF, and stirred at reflux for 4 hr. The mixture was concentrated, and the crude product chromatographed on silica gel with 10% ethyl acetate in dichloromethane. Recrystallization from methanol-water provided the title compound as a white solid, mp 187°–189° C. (10 g, 70%).

Reference Example 9. N,N'-Bis(t-butoxycarbonyl-N"-(3-hydroxyphenyl)methylguanidine.

3-hydroxybenzylamine, prepared as above (1.23 g) and N,N'-bis(tert-butoxycarbonyl)-S-methylisothiourea (2.90 g) were combined in 100 mL DMF, and silver acetate (2.9 g) was added in three portions over 30 min with mechanical stirring. The mixture became thick and a yellow color developed. After 1 hr, the mixture was diluted with 300 mL water, and the solids collected by filtration, re-suspended in dichloromethane, filtered to remove silver salts, and chromatographed on silica gel with 10% ethyl acetate in dichloromethane. Recrystallization provided the title compound as a white solid, mp 169°–172° C. (dec) (2.2 g, 61%).

Reference Example 10. N,N'-Bis(t-butoxycarbonyl)-N"-2-(4-hydroxyphenyl)ethylguanidine.

A solution of N,N'-Bis(tert-butoxycarbonyl)-S-methylisothiourea (22.4 g, 77.3 mmol) is dissolved in 130 mL of THF and added dropwise under nitrogen to 10.6 g (77.3 mmol) of tyramine in 100 mL of THF at 0° C. Reaction reaches completion overnight according to TLC. The solvent is removed in vacuo. Purification on a silica gel column, eluted successively with 5% EtQAc/Hexane, 15% EtOAc/Hexane, and 35% EtOAc/Hexane, provides the title compound as a white solid, m.p. 132°–133° C. (dec.) (21.0 g, 72%).

Reference Example 11. N,N'-Bis(Fbutoxycarbonyl)-N"-3-(4-hydroxyphenyl)propylguanidine.

Silver acetate (1.3 g) was added to a solution of 3-(4-hydroxyphenyl)propylamine hydrochloride (1.2 g) and N,N'-Bis(tert-butoxycarbonyl)-S-methylisothiourea (1.86 g) in DMF (10 mL) containing triethylamine (3.0 g). The mixture was stirred for 3 hr, and an additional 1.0 g silver acetate was added. After one hour, the mixture was diluted with ethyl acetate, filtered through Celite, washed with water, dried over magnesium sulfate, and the solution evaporated. Chromatography on silica gel with 20% ethyl acetate in hexane provided the title compound as a white solid, mp 142°–144° C. (dec) after recrystallization from hexane-ethyl acetate (2.1 g, 77%).

EXAMPLE 1

4-[4-(3,3,3-Triphenylpropanoylamino)phenyl] piperazine.

To an ice cooled and stirred solution of 4-(4-aminophenyl)piperazine (4.29 g, 24.2 mmol) in dichloromethane (100 mL) containing $Et_3N$ (7.42 mL, 52.5 mmol) was added trifluoroacetic anhydride (7.52 mL, 53.2 mmol) in dichloromethane (25 mL) over a 5 minute period. The mixture was allowed to warm to room temperature and stirred two days, then stirred with ice water. The pink solid that separated was isolated by filtration, washed with dichloromethane, aqueous sodium bicarbonate, and water, and dried to obtain 1-(4-(trifluoroacetamido)phenyl)-4-trifluoroacetylpiperazine (4.09 g, 46%, mp 193°–194° C.). To a mixture of this material (0.37 g, 1 mmol) and anhydrous potassium carbonate (1.1 g, 8.0 mmol) in acetonitrile (50 mL) was added 3,3,3-triphenylpropionyl chloride (0.54 g) and the mixture stirred at 80° C. for two days. With tlc monitoring, four additional lots of the acid chloride (4×0.54 g) and potassium carbonate (4×1.1 g) were added at 3 hr intervals, with continued reflux until complete disappearance of the starting piperazine by tlc. The solvent was removed in vacuo, the residue triturated with methanol, the solids removed by filtration and the flitrate evaporated to dryness in vacuo. The residue was stirred with 20% KOH in methanol (15 mL) for 3 hr and then evaporated to dryness in vacuo. The residue was partitioned between water and ethyl acetate and the organic layer extracted with 2N HCl. The acid extract was basified with 2N NaOH to pH 9.5 and extracted with ethyl acetate. The organic layer was washed with brine, then dried over sodium sulfate and evaporated to dryness to give the title compound as a tan solid (0.40 g, 87%), mp 193°–195° C. $^1H$ NMR ($CDCl_3$) δ 7.33 (m,15H), 6.89 (d, J=8.9, 2H) 6.73 (d, J=8.9, 2H), 6.26 (s, 1H), 3.70 (s, 2H), 3.00 (d, J=10.0, 8H). IR 3056, 1665, 1598, 1515, 1447, 1239, 700 $cm^{-1}$. MS 462 (MH+). Anal. calcd. for: $C_{31}H_{31}N_3O.0.5 H_2O$: C, 79.12; H, 6.85; N, 8.93. Found: C, 78.84; H, 6.66; N, 8.64.

EXAMPLE 2

4-[4-(3,3,3-Triphenylpropyloxy)phenyl]-1,2,3,6-tetrahydropiperidine.

To a stirred suspension of NaH (0.088 g of 60% oil dispersion, 2.2 mmol, washed with pentane) in N-methylpyrrolidine (5 mL) under a nitrogen atmosphere, was added 4-(4-hydroxyphenyl)-1,2,3,6-tetrahydropiperidine (0.36 g, 2 mmol) and the mixture heated to 60° for ten minutes until effervescence ceased. To the clear dark solution 3,3,3-triphenylpropyl methanesulfonate in N-methylpyrrolidine (3 mL) was added and the reaction mixture was stirred at 90° C. for two days. Solvent was removed in vacuo at 100° C., and the residue was chromatographed on silica using a gradient of methanol in dichloromethane containing 0.5% triethylamine. The desired product eluted with 10% methanol, and was obtained as an oil (0.26 g, 29%).The hydrochloride salt was prepared by passing gaseous HCl into an isopropanol soution. Recrystallization from isopropanol-ether gave 0.19 g tan powder, softening at 95°–100° C. and melting at 135°–138° C. $^1H$ NMR ($CDCl_3$) δ 9.9 (br s, 2H), 7.33–7.22 (m, 17H), 6.70–6.60 (br m, 2H), 5.86 (s, 1H), 3.73 (t, J=7.5, 4H), 3.12.(t, J=7.2, 4H), 4.0–2.5 (br hump). IR 3400, 2958, 2279, 1607, 1513, 1494, 1447, 1281, 1241, 1183, 1030, 706 cm$^{-1}$. MS 446 (MH$^+$, free base). Anal. calcd. for $C_{32}H_{31}NO.HCl.3H_2O$: C, 71.69; H, 7.14; N, 2.61. Found: C, 71.65; H, 6.53; N, 2.85.

EXAMPLE 3

2-(4-(3,3,3-triphenylpropoxy)pheny)ethylamine.

N-(t-butoxycarbonyl)-2-(4-hydroxyphenyl)ethylamine (1.3 g) and 3,3,3-triphenylpropanol (1.4 g) were coupled by the method of example 5. The product (1.4 g) was dissolved in 15 mL isopropanol containing 1.0 g HCl, and stirred 3 hr at room temperature. A precipitate formed, which was collected and recrystallized from ethanol-ether to provide the hydrochloride salt of the title compound as a white solid, mp 163°–165° C., in 66% yield. Anal. calcd. for $C_{29}H_{29}NO.HCl.0.75\ H_2O$: C, 76.13; H, 6.94; N, 3.06. Found: C, 75.99; H, 6.81; N, 3.02.

EXAMPLE 4

4-(3,3,3-triphenylpropoxy)benzylamine.

By the method of example 3, N-(t-butoxycarbonyl)-4-hydroxybenzylamine was converted into the hydrochloride salt of the title compound, mp 215°–217° C. Anal. calcd. for $C_{28}H_{27}NO.HCl.0.5\ H_2O$: C, 76.61; H, 6.66; N, 3.19. Found: C, 76.86; H, 6.48; N, 3.19.

EXAMPLE 5

N-(2-(4-(3,3,3-triphenylpropoxy)phenyl)ethylguanidine.

A solution of 3,3,3-triphenylpropanol (11.54 g, 40 mmol), N,N'-Bis(t-butoxycarbonyl)-N"-2-(4-hydroxyphenyl)ethylguanidine (15.18 g, 40 mmol), and triphenyphosphine (1.54 g, 44 mmol) in THF (400 mL) was cooled to −15° C., and a solution of diethyl azodicarboxylate (7.66 g, 44 mmol) in 50 mL THF was added dropwise with stirring. The mixture was allowed to warm to room temperature, and then refluxed for 4 hr. The mixture was concentrated, and the residue taken up in toluene (300 mL). Triphenylphosphine oxide was removed by filtration, and the flitrate concentrated and chromatographed on silica gel with dichloromethane. N',N"-bis(t-butoxycarbonyl)-N-(2-(4-(3,3,3-triphenylpropoxy)phenyl)ethylguanidine was obtained as a colorless gum (8.0 g, 31%). This material was dissolved in isopropanol (50 mL) containing anisole (8 g) and anhydrous hydrogen chloride (10 g), and the solution heated until gas evolution was observed, at ca. 50° C. The solution was maintained at this temperature for 15 minutes, then concentrated in vacuo. The residue was stirred vigorously for two days with a mixture of ethyl acetate (200 mL) and 1.0N aqueous sodium bicarbonate, and the resulting white solid collected by filtration, and washed with water, acetone, ethyl acetate, and THF, to provide the bicarbonate salt, containing about 0.75 equivalents of water, as a white powder, mp 172°–176° C. (dec). This material was suspended in 250 mL water, and stirred vigorously while heating to 90° C. Gas evolution was observed, and the solid became gummy for a time, then once again became powdery. When gas evolution had ceased, the mixture was cooled, and the solid collected by filtration and dried in vacuo overnight. The title compound was obtained as the carbonate salt, a white powder, mp 150°–180° C. (dec) with slow heating, 180°–183° C. (dec) with rapid heating. Anal. calcd. for $C_{30}H_{31}N_3O.0.5CH_2O_3$: C, 76.22; H, 6.71; N, 8.74. Found: C, 75.79; H, 6.68; N, 8.87.

EXAMPLE 6

2-(4-(3,3,3-tris(4-chlorophenyl)propoxy)phenyl)ethylamine.

3,3,3-Tris(4-chlorophenyl)propionic acid is reduced to the triarylpropanol with borane as described above. This material is converted by the method of example 3 into the title compound, obtained as the hydrochloride salt, mp 132°–135° C. Anal. calcd. for $C_{29}H_{26}Cl_3NO.HCl.0.25H_2O$: C, 63.12; H, 5.02; N, 2.$3. Found: C, 63.13; H, 4.97; N, 2.55.

EXAMPLE 7

2-(3-(3,3,3-trinhenylpropoxy)phenyl)ethylamine.

By the method of example 3, N-(t-butoxycarbonyl)-2-(3-hydroxyphenyl)ethylamine was converted to the title compound, and was then converted to the oxalate salt by combining with oxalic acid in ether. Recrystallization from ethyl acetate-ether provided the title compound as the 0.5 oxalate 0.5 hydrate, a white solid, mp 166°–168° C. $^1$H NMR (DMSO-d$_6$) δ 7.2–7.4 (m, 15H), 7.12 (t, J=7 Hz, 1H), 6.74 (d, J=7 Hz, 1H), 6.5–6.6 (m, 2H), 4.5–5.5 (br s, 4H, —NH$_3^+$ and HOD), 3.66 (t, J=7 Hz, 2H), 3.07 (t, J=7 Hz, 2H), 2.85 (t, J=7 Hz, 2H), 2.65 (t, J=7 Hz, 2H), Anal. calcd. for $C_{29}H_{29}NO.0.5C_2H_2O_4.0.5H_2O$: C, 78.06; H, 6.77; N, 3.03. Found: C, 78.26; H, 6.73; N, 3.13.

EXAMPLE 8

2-(4-methoxy-3-(3,3,3-triphenylpropoxy)phenyl)ethylamine.

Di-t-butyl dicarbonate (1.15 g, 5.25 mmol) was added to a mixture of 3-hydroxy-4-methoxyphenethylamine hydrochloride (1.05 g, 5.15 mmol) and triethylamine (0.521 g, 5.15 mmol) in water (1 mL), dimethylformamide (5 mL) and dichloromethane (25 mL). The mixture was stirred at room temperature overnight. The organic phase was transferred directly to a silica gel column packed in dichloromethane, and eluted with dichloromethane, then with 10% ethyl acetate in dichlorornethane. Evaporation the eluate provided N-(t-butoxycarbonyl)-2-(3-hydroxy-4-methoxyphenyl)ethylamine, as a white solid, mp 100°–101° C., after trituration with hexane. By the method of example 3, this was converted into the title compound, obtained as the hydrochloride salt, a white solid, mp 111°–112° C. $^1$H NMR (DMSO-d$_6$) δ 7.84 (s, 3H, —NH$_3^+$), 7.2–7.4 (m, 15H), 6.88 (d, J=8 Hz, 1 H), 6.74 (dd, J=1 and 8 Hz, 1H), 6.46 (d, J=1 Hz, 1H), 3.72 (s, 3H), 3.66 (t, J=7 Hz, 2H), 3.08 (t, J=7 Hz, 2H), 2.90 (t, J=7 Hz, 2H), 2.68 (t, J=7 Hz, 2H), Anal. calcd. for $C_{30}H_{31}NO_2.HCl.0.25\ H_2O$: C, 75.30; H, 6.85; N, 2.93. Found: C, 75.10; H, 6.74; N, 2.80.

EXAMPLE 9

N-(2-(4-(3,3,3-tris(4-chlorophenyl)propoxy)phenyl)ethyl)guanidine

By the method of example 5, 3,3,3-Tris(4-chlorophenyl) propanol is converted into the title compound, obtained as the bicarbonate salt, a white solid, mp 146°–150° C. $^1$H NMR (DMSO-d$_6$) δ 7.39 (d, J=8.7 Hz, 6H), 7.28 (d, J=8.7 Hz, 6H), 7.07 (d, J=8.5 Hz, 2H), 6.62 (d, J=8.5 Hz, 2H), 3.64 (t, J=7 Hz, 2H), 3.05 (t, J=7 Hz, 2H), 3.1–3.5 (br m, 6H), 2.63 (t, J=7 Hz, 2H). Anal. calcd. for $C_{30}H_{28}Cl_3N_3O \cdot CH_2O_3$: C, 60.55; H, 4.92; N, 6.83. Found: C, 60.93; H, 4.80; N, 6.90.

EXAMPLE 10

N-(2-(4-(5,5,5-triphenylpentoxy)phenyl) ethylguanidine

By the method of example 5, 5,5,5-triphenyl-1-pentanol is converted into the title compound, obtained as the oxalate salt, a white solid, mp 119°–121° C. Anal. calcd. for $C_{32}H_{35}N_3O \cdot C_2H_4O_4 \cdot 0.5H_2O$: C, 70.57; H, 6.97; N, 7.26. Found: C, 70.41; H, 6.63; N, 7.18.

EXAMPLE 11

N-(2-(4-(4,4,4-triphenylbutoxy)phenyl) ethylguanidine

By the method of example 5, 4,4,4-triphenyl-1-butanol is converted into the title compound, obtained as the bicarbonate salt, a white solid, mp 169°–170° C. Anal. calcd. for $C_{31}H_{33}N_3O \cdot CH_2O_3 \cdot 0.5H_2O$: C, 71.89; H, 6.79; N, 7.86. Found: C, 71.59; H, 6.64; N, 7.71.

EXAMPLE 12

3-[4-(3,3,3-Triphenylpropoxy)phenyl]propionic acid.

To a solution of 3,3,3-triphenylpropanol (2.22 g, 7.70 mmol), methyl 3-(4-hydroxyphenyl)propionate (9.40 mmol) and triphenylphosphine (2.42 g, 9.23 mmol) in dry THF (25 mL) under a nitrogen atmosphere at room temperature, was added dropwise DEAD (1.50 mL, 9.52 mmol) in dry THF (20 mL) over approximately 30 minutes. The reaction was heated to reflux overnight. After cooling, the THF was evaporated and the residue chromatographed on a silica column with 5–15% EtOAc/hexanes to afford the ester as snow white crystals, mp=53°–54° C. (triturated with hexanes), 67% yield. $^1$H NMR (CDCl$_3$) δ 7.19–7.33 (m, 15H), 7.02 (d, J=8.7 Hz, 2H), 6.62 (d, J=8.7 Hz, 2H), 3.68 (t, J=7.8 Hz, 2H), 3.64 (s, 3H), 3.12 (t, J=7.8 Hz, 2H), 2.84 (t, J=7.7 Hz, 2H), 2.55 (t, J=7.7 Hz, 2H). IR 3064, 1737, 1512, 1238 cm$^{-1}$. MS 451 (MH+), 271 (base). Anal. calcd. for $C_{31}H_{30}O_3$: C, 82.64; H, 6.71. Found: C, 82.72; H, 6.77. This ester (667 mg, 1.49 mmol) and NaOH (1N, 3.0 mL) in methanol (10 mL) were heated to 60° C. overnight. After cooling, the methanol was evaporated. The resulting aqueous residue was diluted with water (20 mL) and acidified to pH=1 with conc HCl. The precipitate was collected, washed with water (50 mL) and dried in vacuo. White solid, mp=126°–127° C. (ether/hexanes), 89.5% yield. $^1$H NMR (CDCl$_3$) δ 7.02–7.25 (m, 15H), 6.95 (d, J=8.3 Hz, 2H), 6.55 (d, J=8.3 Hz, 2H), 3.62 (t, J=7.6 Hz, 2H), 3.04 (t, J=7.6 Hz, 2H), 2.76 (t, J=7.6 Hz, 2H), 2.51 (t, J=7.6 Hz, 2H). IR 2880–3160 (br), 1690 cm$^{-1}$. MS 437 (MH+). Anal. calcd. for $C_{30}H_{28}O_3 \cdot 0.2H_2O$: C, 81.86; H, 6.50. Found: 81.76; H, 6.45.

EXAMPLE 13

2-[4-(3,3,3-Triphenylpropoxy)phenyl]acetic acid.

By the method of example 12, methyl (4-hydroxyphenyl) acetate was converted to the title compound. White solid, mp=148°–149° C. (ether), 72% yield. $^1$H NMR (CDCl$_3$) δ 7.19–7.34 (m, 15H), 7.10 (d, J=8.6 Hz, 2H), 6.65 (d, J=8.6 Hz, 2H), 3.70 (t, J=7.8 Hz, 2H), 3.54 (s, 2H), 3.12 (t, J=7.8 Hz, 2H). IR 3100–2800 (br), 1709, 1514 cm$^{-1}$. MS 423 (MH+), 243. Anal. calcd. for $C_{29}H_{26}O_3$: C, 82.44; H, 6.20. Found: C, 82.17; H, 6.30.

EXAMPLE 14

3-[4-(3,3,3-Triphenylpropylthio)phenyl]propionic acid.

By the method of example 12, but using ADDP instead of DEAD, and n-Bu$_3$P instead of Ph$_3$P, methyl 4-mercaptohydrocinnamate was converted into the title compound. Colorless solid, mp=51°–53° C., 67% yield. $^1$H NMR (CDCl$_3$) δ 9.50 (br s, 1 H), 7.08–7.45 (m, 19H), 2.84 –2.92 (m, 4H), 2.57–2.61 (m, 4H). IR 3500, 1707, 1594, 1492, 1290 cm$^{-1}$. MS 453 (MH+). Anal. calcd. for $C_{30}H_{28}O_2S$: C, 79.61; H, 6.24. Found: C, 79.29; H, 5.87.

EXAMPLE 15

4-[4-(3,3,3-Triphenylpropoxy)phenyl]butyric acid.

By the method of example 12, methyl 4-(4-hydroxyphenyl)butyrate was converted to the title compound, obtained as an amorphous solid containing residual ethyl acetate. $^1$H NMR (CDCl$_3$) δ 7.17–7.34 (m, 15H), 7.00 (d, J=8.6 Hz, 2H), 6.62 (d, J=8.6 Hz, 2H), 3.69 (t, J=7.8 Hz, 2H), 3.12 (t, J=7.8 Hz, 2H), 2.56 (t, J=7.5 Hz, 2H), 2.32 (t, J=7.5 Hz, 2H), 1.89 (quin., J=7.5 Hz, 2H). IR 3300–2500 (br), 1711, 1512 cm$^{-1}$. MS 451 (MH+), 243. Anal. calcd. for $C_{31}H_{30}O_3 \cdot 0.05C_4H_8O_2$: C, 82.36; H, 6.73. Found: C, 82.02; H, 6.71.

EXAMPLE 16

N-[4-(2-Aminoethyl)phenyl]-3,3,3-triphenylpropionamide.

To 3,3,3-triphenylpropanoic acid (1.0 g, 3.3 mmol) in dry benzene (10 mL) under a nitrogen atmosphere at room temperature, was added DMF (2 drops) followed by oxalyl chloride (0.29 mL; 3.3 mmol). After stirring for 1 h, the benzene was evaporated to give acid chloride (1.02 g, 96% yield). To the acid chloride (300 mg; 0.94 mmol) in dichloromethane (15 mL) at 0° C. under a nitrogen atmosphere, was added triethylamine (0.26 mL; 1.87 mmol). N-(t-butoxycarbonyl)-2-(4-hydroxyphenyl)ethylamine (0.94 mmol) in dichloromethane (5 mL) was added dropwise over a 10 minute period. After stirring overnight, the reaction was poured into brine (25 mL) and extracted with EtOAc (2×50 mL). The combined organic layers were washed with water (25 mL), brine (25 mL), dried (MgSO$_4$), filtered and evaporated. Off-white solid, mp=179°–181° C. (ethanol). $^1$H NMR δ 7.26–7.34 (m, 15H), 6.99 (d, J=8.5 Hz, 2H), 6.90 (d, J=8.5 Hz, 2H), 6.34 (s, 1H), 4.45 (br s, 1H), 3.72 (s, 2H), 3.28 (m, 2H), 2.68 (t, J=7.6 Hz, 2H), 1.37 (s, 9H). IR 2900–3400 (br), 1678, 1531 cm$^{-1}$. MS 521 (MH+). Anal. calcd. for $C_{34}H_{36}N_2O_3 \cdot 0.2H_2O$: C, 77.89; H, 7.00; N, 5.34. Found: C, 77.64; H, 6.91; N, 5.24. The protected amine (0.50 mmol) was dissolved in 20% HCl in isopropanol (5 mL) and heated to 80° C. for 30 min. After cooling, the precipitate was collected by filtration, washed with isopropanol, and dried in vacuo. The title compound was obtained as the hydrochloride monohydrate, a white solid, mp>250° C. (ethanol), in 69% yield. $^1$H NMR (DMSO-d$_6$) δ 9.65 (br s, 1H), 7.82 (br s, 3H), 7.16–7.25 (m, 17H), 7.06 (d, J=8.5 Hz, 2H), 3.83 (s, 2H), 2.92–2.95 (m, 2H), 2.74–2.77 (m, 2H). IR 2800–3480 (br), 1664, 1515 cm$^{-1}$. MS 421 (MH+), 243. Anal. calcd. for $C_{29}H_{28}N_2O \cdot HCl \cdot H_2O$: C, 73.33; H, 6.58; N, 5.90. Found: C, 73.22; H, 6.56; N, 5.92.

EXAMPLE 17

6-(3,3,3-Triphenylpropoxy)-2-naphthoic acid.

6-(3,3,3-Triphenylpropoxy)-2-naphthonitrile, prepared in example 20, was added to KOH (1 g) dissolved in ethanol (15 mL). The solution was heated at reflux under a nitrogen atmosphere for two days. After cooling, the ethanol was evaporated and the residue diluted with water. This was acidified with dilute HCl and extracted with dichloromethane. The organic layers were washed with water, dried (MgSO$_4$), filtered and evaporated, providing the title compound as a colorless solid, mp=243°–244° C. (Et$_2$O/ pentane), 68% yield. $^1$H NMR (CDCl$_3$) δ 8.58 (s, 1H), 8.02 (m, 1H), 7.82 (d, J=9.0, 1H), 7.64 (d, J=8.7, 1H), 7.20–7.38 (m, 15H), 7.11 (dd, J=2.3, 9.0 Hz, 1H), 6.80 (m, 1H), 3.91 (m, 2H), 3.21 (m, 2H). MS 459 (MH$^+$). Anal. calcd. for C$_{32}$H$_{26}$O$_3$: C, 83.82; H, 5.72. Found: C, 83.69; H, 5.63.

EXAMPLE 18

N-[4-(2-Guanidinoethyl)phenyl]-3,3,3-triphenylpropionamide.

By the method of example 16, N,N'-bis(t-butoxycarbonyl)-N''-2-(4-hydroxyphenyl)ethylguanidine was converted to the title compound, obtained as the bis-hydrochloride salt, a yellow solid, mp=213°–215° C., 81% yield. $^1$H NMR (DMSO-d$_6$) δ 7.39–7.44 (m, 1H), 7.17–7.25 (m, 17H), 7.07 (d, J=8.5 Hz, 2H), 3.82 (s, 2H), 3.20–3.27 (m, 2H), 2.61–2.66 (m, 2H). IR 2800–3400 (br), 1659, 1516 cm$^{-1}$. MS 463 (MH+). Anal. calcd. for C$_{30}$H$_{30}$N$_4$O.2HCl: C, 67.29; H, 6.02; N, 10.46. Found: C, 67.46; H, 6.16; N, 10.95.

EXAMPLE 19

4,5-Dihydro-2-{2-[4-(3,3,3-triphenylpropoxy)phenyl]ethyl}oxazole.

By the method of example 25, ethanolamine was converted to N-(2-hydroxyethyl)-3-[4-(3,3,3-triphenylpropoxy)phenyl]propionamide. To this amide (400 mg; 0.84 mmol) in EtOAc (15 mL), was added dropwise over 5 minutes thionyl chloride (0.20 mL, 2.74 mmol) in EtOAc (2 mL) under a nitrogen atmosphere at room temperature. After stirring overnight, the precipitate was collected and washed with EtOAc to give the title compound (354.1 mg; 85% yield) as the hydrochloride monohydrate, a white powder. mp=130°–131° C. $^1$H NMR δ 7.19–7.34 (m, 15H), 7.02 (d, J=8.6 Hz, 2H), 6.62 (d, J=8.6 Hz, 2H), 3.70 (t, J=7.7 Hz, 2H), 3.53 (br s, 4H), 3.12 (t, J=7.7 Hz, 2H), 2.87 (t, J=7.5 Hz, 2H), 2.43 (t, J=7.5 Hz, 2H). IR 2954, 1513, 1245 cm$^{-1}$. MS 462 (MH+), 243. Anal. calcd. for C$_{32}$H$_{31}$NO$_2$.HCl.H$_2$O: C, 74.48; H, 6.48; N, 2.71. Found: C, 74.26; H, 6.32; N, 2.70.

EXAMPLE 20

6-(3,3,3-Triphenylpropoxy)-2-naphthylmethylamine.

6-(3,3,3-Triphenylpropoxy)-2-naphthonitrile was prepared by the method of example 27 utilizing 6-cyano-2-naphthol, ADDP, and nBu$_3$P. Colorless solid, mp=207°–208° C. (Et$_2$O/hexane), 50% yield. $^1$H NMR (CDCl$_3$) δ 8.09 (s, 1H), 7.72 (d, J=9.0, 1H), 7.63 (s, 1H), 7.50 (dd, J=1.4 and 8.5 Hz, 1H), 7.20–7.37 (m, 16H), 6.76 (d, J=2.1, 1H), 3.90 (m, 2H), 3.20 (m, 2H). IR 2220, 1621, 1602, 1493, 1472, 1396 cm$^{-1}$. MS 440 (MH$^+$). Anal. calcd. for C$_{32}$H$_{25}$NO: C, 87.44; H, 5.73; N, 3.19. Found: C, 86.93; H, 5.78; N, 3.09. A mixture of the nitrile (0.440 g, 1 mmol) and tetra-n-butylammonium borohydride (0.775 g, 3 mmol) in dichloromethane was heated to reflux under an atmosphere of nitrogen for 18 h. The solvent was removed in vacuo and the residue treated with 10% HCl and refluxed for 3 h. The reaction mixture was then basified with solid NaOH and the liberated amine was extracted in dichloromethane/ benzene. The organic extracts were washed with water, dried (Na$_2$SO$_4$), filtered and evaporated to dryness to obtain a solid residue which was converted to the hydrochloride salt by passing dry HCl gas into a dichloromethane solution and recrystallizing from dichloromethane/Et$_2$O to obtain 0.210 g (44%), mp=137–140. $^1$H NMR (CDCl$_3$) δ8.44 (s, 2H, exchangeable), 7.10–7.47 (m, 19 H), 6.49 (dd, J=2.1 and 8.9 Hz, 1H), 6.44 (d, J=1.7, 1H), 3.72 (s, 2H), 3.66 (m, 2H), 3.05 (m, 2H). IR 3422 –2600, 1634, 1607, 1490, 1475 cm$^{-1}$. MS 444 (MH$^+$). Anal. calcd. for: C$_{32}$H$_{29}$NO.HCl.0.2 H$_2$O: C, 79.32; H, 6.34; N, 2.89. Found: C, 79.28; H, 6.41; N, 2.92.

EXAMPLE 21

4-(3,3,3-Triphenylpropoxy)benzoic acid.

By the method of example 12, methyl 4-hydroxybenzoate was converted to the title compound. White solid, mp=201°–202° C. (MeOH/H$_2$O), 67% yield. $^1$H NMR (DMSO-d$_6$) δ 7.72 (d, J=8.6 Hz, 2H), 7.20–7.36 (m, 15H), 6.57 (d, J=8.6 Hz, 2H), 3.67 (t, J=7.3 Hz, 2H), 3.00 (t, J=7.3 Hz, 2H). IR 2640–3172 (br), 1674, 1602 cm$^{-1}$. MS 409 (MH+), 243. Anal. calcd. for C$_{28}$H$_{24}$O$_3$: C, 82.33; H, 5.92. Found: C, 82.04; H, 5.91.

EXAMPLE 22 trans 4-(3,3.3-Triphenylpropoxy)cinnamic acid.

By the method of example 12, methyl 4-hydroxycinnamate was converted to the title compound. White crystals, mp=207°–209° C. (EtOAc/hexanes), 90% yield. $^1$H NMR (CDCl$_3$) δ 7.68 (d, J=15.9 Hz, 1H), 5 7.41 (d, J=8.8 Hz, 2H), 7.20–7.34 (m, 15H), 6.69 (d, J=8.8 Hz, 2H), 6.27 (d, J=15.9 Hz, 1H), 3.75 (t, J=7.7 Hz, 2H), 3.14 (t, J=7.7 Hz, 2H). IR 2900–3400 (br), 1688, 1624, 1602, 1173 cm$^{-1}$. MS 435 (MH+), 243 (base). Anal. calcd. for C$_{30}$H$_{26}$O$_3$.0.2 H$_2$O: C, 82.24; H, 6.07. Found: C, 82.31; H, 6.05.

EXAMPLE 23

3,3,3-Triphenylpropyl 2-(4-hydroxyphenyl)acetate.

To triphenylpropanol (3.98 mmol), 4-hydroxyphenylacetic acid (3.98 mmol), and triphenylphosphine (4.39 mmol) in dry THF (20 mL) at 0° C. under a nitrogen atmosphere, was added DEAD (4.39 mmol) in dry THF (20 mL) over 15 minutes. The reaction was stirred at room temperature for 16 h and then the THF was evaporated. The residue was chromatographed on silica gel using 15–30% EtOAc/hexanes. White solid, mp=136°–138° C. (ether), 34% yield. $^1$H NMR δ 7.15–7.27 (m, 15H), 7.10 (d, J=8.5 Hz, 2H), 6.77 (d, J=8.5 Hz, 2H), 4.90 (s, 1H), 3.90 (t, J=7.9 Hz, 2H), 3.47 (s, 2H), 2.93 (t, J=7.9 Hz, 2H). Anal. calcd. for C$_{29}$H$_{26}$O$_3$: C, 82.44; H, 6.20. Found: C, 82.29; H, 6.24.

EXAMPLE 24

3,3,3-Triphenylpropyl 3-(4-hydroxyphenyl) propionate.

By the method of example 23, 3-(4-hydroxyphenyl) propionic acid was converted to the title compound. Light yellow solid, mp=105°–107° C., 29% yield. $^1$H NMR δ 7.15–7.30 (m, 15H), 7.05 (d, J=8.5 Hz, 2H), 6.75 (d, J=8.5 Hz, 2H), 4.64 (s, 1 H, exchangeable), 3.87 (t, J=7.9 Hz, 2H), 2.81–2.91 (m, 4H), 2.51 (t, J=7.8 Hz, 2H). IR 3100–3600 (br), 1882 cm$^{-1}$. MS 437 (MH+). Anal. calcd. for $C_{30}H_{28}O_3$: C, 82.54; H, 6.46. Found: C, 82.09; H, 6.45.

EXAMPLE 25 trans N-(2-Hydroxyethyl)-4-(3,3,3-triphenylpropoxy)cinnamide.

By the method of example 22, methyl 4-(3,3,3-triphenylpropoxy)cinnamate was prepared. This ester (500 mg; 1.11 mmol) and ethanolamine (1.5 mL) were heated in an oil bath at 100° C. for 3.5 h under a nitrogen atmosphere. After cooling, the reaction was poured into water (100 mL) and extracted with EtOAc (3×75 mL). The organic layers were washed with water (100 mL), dried (MgSO$_4$), filtered and evaporated to give the title compound as a hemihydrate, a white, fluffy solid, mp=215°–216° C., 60% yield. $^1$H NMR δ 7.53 (d, J=15.5 Hz, 1H), 7.15–7.37 (m, 17H), 6.65 (d, J=8.9 Hz, 2H), 6.25 (d, J=15.5 Hz, 1H), 6.22 (br s, 1H), 3.70–3.77 (m, 4H), 3.50–3.55 (m, 2H), 3.12 (t, J=7.7 Hz, 2H). IR 3000–3250 (br), 1662, 1624, 1603, 1512 cm$^{-1}$. MS 478 (MH+). Anal. calcd. for $C_{32}H_{31}NO_3 \cdot 0.5H_2O$: C, 78.99; H, 6.63; N, 2.28. Found: C, 79.1 0; H, 6.54; N, 2.81.

EXAMPLE 26

4,5-Dihydro-2-{2-[4-(3,3,3-triphenylpropoxy)phenyl]ethyl}-1,3-oxazine.

By the method of example 19, 3-amino-1-propanol was converted into the title compound, obtained as the hydrochloride salt, an amorphous solid, mp=60°–63° C. (EtOAc), 78% yield. $^1$H NMR (DMSO-d$_6$) δ 7.84 (m, 1H), 7.19–7.38 (m, 15H), 6.99 (d, J=8.6 Hz, 2H), 6.56 (d, J=8.6 Hz, 2H), 3.63 (t, J=7.6 Hz, 2H), 3.51 (t, J=6.8 Hz, 2H), 3.00–3.18 (m, 4H), 2.68 (t, J=7.5 Hz, 2H), 2.28 (t, J=7.5 Hz, 2H), 1.77 (quin, J=6.8 Hz, 2H). IR 3030–3300 (br), 1643, 1611, 1511 cm$^{-1}$. MS 476 (MH+), 243. Anal. calcd. for $C_{33}H_{33}NO_2 \cdot HCl \cdot 0.5\ H_2O$: C, 76.06; H, 6.77; N, Z.69. Found: C, 75.98; H, 6.60; N, 2.65.

EXAMPLE 27.

5-{2-[4-(3,3,3-Triphenylpropoxy)phenyl]ethyl}-1H-tetrazole.

To 3,3,3-triphenylpropanol (8.70 mmol), 3-(4-hydroxyphenyl)propionitrile (9.40 mmol) and triphenylphosphine (2.42 g, 9.23 mmol) in dry THF (25 mL) under a nitrogen atmosphere at room temperature, was added dropwise DEAD (1.50 mL, 9.52 mmol) in dry THF (20 mL) over approximately 30 minutes. The reaction was heated to reflux overnight. After cooling, the THF was evaporated and the residue chromatographed on a silica column, with 15–20% EtOAc/hexanes. White solid, mp=98°–100° C. (ether), 60% yield. $^1$H NMR δ 7.18–7.35 (m, 15H), 7.06 (d, J=8.6 Hz, 2H), 6.67 (d, J=8.6 Hz, 2H), 3.72 (t, J=7.8 Hz, 2H), 3.13 (t, J=7.8 Hz, 2H), 2.85 (t, J=7.3 Hz, 2H), 2.54 (t, J=7.3 Hz, 2H). IR 2243, 1540 cm$^{-1}$. MS 418 (MH+), 243. Anal. calcd. for $C_{30}H_{27}NO$: C, 86.30; H, 6.52; N, 3.35. Found: C, 86.07; H, 6.39; N, 3.24. To a solution of trimethyl aluminum (1M in hexanes, 0.57 mL), in toluene (3 mL) at ~2° C., was added azidotrimethylsilane (0.569 mmol). A solution of nitrile (0.474 mmol) in toluene (2 mL) was slowly added. The reaction was stirred at 80° C. for 72 h. The cooled (0° C.) reaction was added dropwise to HCl (6M, 10 mL) and EtOAc (10 mL). The resulting mixture was extracted with EtOAc (2×50 mL). The combined organic layers were dried (MgSO$_4$), filtered and evaporated. The crude material was triturated with dichloromethane to remove unreacted starting nitrile leaving behind the title compound as a hydrate, a white solid (mp=193°–195° C., 30% yield). $^1$H NMR (DMSO-d$_6$) δ 7.19–7.35 (m, 15H), 7.02 (d, J=8.5 Hz, 2H), 6.58 (d, J=8.5 Hz, 2H), 3.60 (t, J=7.4 Hz, 2H), 3.04–3.12 (m, 4H), 2.91 (t, J=7.6 Hz, 2H). IR 3300–3450 (br), 1586, 1511 cm$^{-1}$. MS 461 (MH+), 243. Anal. calcd. for $C_{30}H_{28}N_4O \cdot 0.25H_2O$: C, 77.48; H, 6.18; N, 12.05. Found: C, 77.18; H, 5.96; N, 11.71.

EXAMPLE 28

N-Benzyl-N,N-dimethyl-[4-(3,3,3-triphenylpropoxy)phenyl]methyl ammonium chloride.

By the method of example 12, 4-hydroxybenzaldehyde was condensed with 3,3,3-triphenylpropanol to provide 4-(3,3,3-triphenylpropoxy)benzaldehyde, a white solid, mp 127°–130° C. after recrystallization from hexane (58% yield). This material (4.0 g, 10.2 mmol) was suspended in ethanol (100 mL), and sodium borohydride (0.2 g, 5.0 mmol) was added. After 3 hr, aqueous 1N HCl was added dropwise until gas evolution ceased. Precipitated boric acid was removed by filtration, and the flitrate concentrated to a gummy residue. This was partitioned between water and ether, and the ether solution dried (MgSO$_4$), filtered, and concentrated. The residue was kept under high vacuum overnight to remove solvent, leaving 4-(3,3,3-triphenylpropoxy)benzyl alchohol as an amorphous solid (3.9 g, 97%). This material (3.9 g, 9.9 mmol) was dissolved in benzene (80 mL), and thionyl chloride (1.0 mL, 14 mmol) was added, followed by five drops of DMF at 5-minute intervals. The mixture was heated briefly to reflux, cooled, and concentrated to an oil which solidified on standing. Trituration of the solid with cold methanol provided 4-(3,3,3-triphenylpropoxy)benzyl chloride as a white powder, mp 91°–95° C. (83%). $^1$H NMR (CDCl$_3$) δ 7.19–7.35 (m, 17H), 6.66 (d, J=8.7 Hz, 2H), 4.51 (s, 2H), 3.72 (t, J=7.8 Hz, 2H), 3.12 (t, J=7.8 Hz, 2H).

A solution of this material (250 mg, 0.60 mmol) and benzyldimethylamine (85 mg, 0.63 mmol) in acetonitrile (10 mL) was heated to 80° C. for 24 hr. A solid formed on cooling which was collected, recrystallized from acetonitrile, and dried at 90° C. under high vacuum. The title compound was obtained as a hemihydrate, a white powder, mp 195°–197° C. (dec), in 39% yield. $^1$H NMR (CDCl$_3$) δ 7.61 (dd, J=ca. 8 Hz and ca. 1 Hz, 2H), 7.46 (d, J=8.7 Hz, 2H), 7.43–7.20 (m, 18H), 6.70 (d, J=8.7 Hz, 2H), 5.03 (s, 2H), 4.99 (s, 2H), 3.72 (t, J=7.7 Hz, 2H), 3.12 (t, J=7.7 Hz, 2H), 3.05 (s, 6H). Anal. calcd. for $C_{37}H_{38}NO \cdot Cl \cdot 0.5H_2O$: C, 79.76; H, 7.06; N, 2.51; Cl, 6.36. Found: C, 79.83; H, 7.02; N, 2.49; Cl, 6.47.

EXAMPLE 29

1-{[4-(3,3,3-triphenylpropoxy)phenyl]methyl}pyridinium chloride.

A solution of 4-(3,3,3-triphenylpropoxy)benzyl chloride, prepared in example 28, (210 mg, 0.51 mmol) in pyridine (1.0 mL) was refluxed for two minutes, and concentrated. The residue was recrystallized from acetonitrile-ethyl acetate and dried at 90° under high vacuum for 18 hours, providing the title compound as a monohydrate, a white powder, mp 155°–159° C. (212 mg, 86%). $^1$H NMR (CDCl$_3$) δ 9.56 (d, J=7.5 Hz, 2H), 8.31 (t, J=7.5 Hz, 1H), 7.94 (t, J=7.5 Hz, 2H), 7.54 (d, J=8.6 Hz, 2H) 7.15–7.35 (m, 15H), 6.68 (d, J=8.6 Hz, 2H), 3.68 (t, J=7.7 Hz, 2H), 3.09 (t, J=7.7 Hz, 2H). Anal. calcd. for C$_{33}$H$_{30}$NO.Cl.H$_2$O: C, 77.71; H, 6.32; N, 2.75; Cl, 6.95. Found: C, 77.47; H, 6.27; N, 2.63; Cl, 6.65.

EXAMPLE 30

1,2-Dimethyl-3-{[4-(3,3,3-triphenylpropoxy)phenyl]methyl}imidazolium chloride.

A solution of 4-(3,3,3-triphenylpropoxy)benzyl chloride, prepared in example 28, (210 mg, 0.51 mmol) and 1,2-dimethylimidazole (50 mg, 0.52 mmol) in acetonitrile (2 mL) was heated to 80° C. for 18 hr. The mixture was cooled, and ethyl acetate (1 mL) was added. Crystallization was induced by scratching with a glass rod, and additional ethyl acetate (5 mL) was added. The mixture was heated to reflux, cooled, and the precipitate collected by filtration. Attempts to remove solvent and water by prolonged heating at 90° C. in vacuo resulted in gradual loss of chlorine. The material was dissolved in ethanol (0.5 mL), and the solution diluted with aqueous 1N HCl (10 mL). The precipitate was collected and dried for 2 hr at 70° under high vacuum, to provide the title compound as a hydrate: shiny white flakes, losing water and/or chloromethane at 140° C., and melting at 193°–196° C. $^1$H NMR (CDCl$_3$) δ 7.58 (d, J=2.0 Hz, 1H), 7.43 (d, J=2.0 Hz, 1H) 7.15–7.35 (m, 17H), 6.68 (d, J=8.6 Hz, 2H), 5.37 (s, 2H), 3.95 (s, 3H), 3.68 (t, J=7.7 Hz, 2H), 3.09 (t, J=7.7 Hz, 2H), 2.78 (s, 3H). Anal. calcd. for C$_{33}$H$_{33}$N$_2$O.Cl.1.3H$_2$O: C, 74.43; H, 6.74; N, 5.26; Cl, 6.66. Found: C, 74.64; H, 6.89; N, 5.21; Cl, 6.41.

EXAMPLE 31

[4-(3,3,3-Triphenylpropoxy)benzylidene]malonic acid.

To triphenylpropanol (6.21 g; 21.53 mmol), p-hydroxybenzaldehyde (3.43 g; 28.08 mmol) and triphenylphosphine (6.88 g; 26.23 mmol) in dry THF (75 mL) under a nitrogen atmosphere at room temperature, was added dropwise over a 30 minute period DEAD (4.2 mL; 26.67 mmol) in dry THF (50 mL). The reaction was heated at reflux for two days. After cooling, the solvent was evaporated in vacuo and the residue chromatographed on a silica column using 5% EtOAc/hexanes. The aldehyde (5.40 g; 64.0% yield) was isolated as white crystals. mp=129°–130° C. $^1$H NMR (CDCl$_3$) δ 9.83 (s, 1H), 7.74 (d, J=8.7 Hz, 2H), 7.19–7.34 (m, 15H), 6.76 (d, J=8.7 Hz, 2H), 3.82 (t, J=7.7 Hz, 2H), 3.16 (t, J=7.7 Hz, 2H). IR 3030, 1689, 1594 cm$^{-1}$. MS 393 (MH+), 243. Anal. calcd. for C$_{28}$H$_{24}$O$_2$: C, 85.68; H, 6.16. Found: C, 85.30; H, 6.22. A mixture of the benzaldehyde (235 mg, 0.5990 mmol) and malonic acid (84 mg; 0.810 mmol) in glacial HOAc (1 mL) was heated in an oil bath at 80° C. under a nitrogen atmosphere for 16 h. The resulting white precipitate was collected and washed with water. Recrystallization from methanol/water afforded the title compound as a white solid (205 mg; 72% yield) mp=208°–209° C. (dec). $^1$H NMR (DMSO-d$_6$) δ 7.48 (d, J=8.5 Hz, 2H), 7.42 (s, 1H), 7.20–7.38 (m, 15H), 6.75 (d, J=8.5 Hz, 2H), 3.76 (t, J=7.6 Hz, 2H), 3.11 (t, J=7.6 Hz, 2H). $^{13}$C NMR (DMSO-d$_6$) δ 170.0, 167.2, 161.8, 148.2, 140.1 (CH), 133.0 (CH), 130.4 (CH), 129.8 (CH), 127.8 (CH), 127.3, 127.0, 116.4 (CH), 67.3 (CH$_2$), 56.6, 40.1 (CH$_2$). IR 2965–3400 (br), 1733, 1632, 1598, 1510 cm$^{-1}$. MS 435 (MH+—CO$_2$H), 243 (base). Anal. calcd. for C$_{31}$H$_{26}$O$_5$: C, 77.81; H, 5.48. Found: C, 77.52; H, 5.51.

EXAMPLE 32

5-[4-(3,3,3-Triphenylpropoxy)phenyl]methyl-1H-tetrazole.

By the method of example 27, 4-hydroxyphenylacetonitrile was converted to the intermediate nitrile. To the nitrile (3.47 mmol) in DMF (20 mL) under a nitrogen atmosphere at room temperature, was added ammonium chloride (10.4 mmol) followed by sodium azide (10.4 mmol). After a catalytic amount of lithium chloride (0.10 weight of nitrile) was added, the reaction was heated to 135° C. for 24 h. The solvent was removed in vacuo. The reaction was diluted with water (50 mL), made basic with aqueous NaOH (1N), and then acidified to pH=1 with HCl (1.0N). The aqueous layer was extracted with EtOAc (3×150 mL). The combined organic layers were washed with water (3×50 mL), dried (MgSO$_4$), filtered and evaporated. Light yellow solid, mp=187°–189° C. (recrystallized from MeOH/H$_2$O, 80% yield). $^1$H NMR (DMSO-d$_6$) δ 7.21–7.34 (m, 15H), 7.10 (d, J=8.6 Hz, 2H), 6.64 (d, J=8.6 Hz, 2H), 4.15 (s, 2H), 3.58–3.64 (m, 2H), 3.00–3.07 (m, 2H). IR 3200–3400 (br), 1609, 1510 cm$^{-1}$. MS 447 (MH+), 243. Anal. calcd. for C$_{29}$H$_{26}$N$_4$O: C, 78.00; H, 5.87; N, 12.55. Found: C, 77.60; H, 5.82; N, 12.13.

EXAMPLE 33

N,N,N-Trimethyl-[4-(3,3,3-triphenylpropoxy)phenyl]methylammonium chloride.

A suspension of 4-(3,3,3-triphenylpropoxy)benzyl chloride, prepared in example 28, (413 mg, 1.0 mmol) in commercial 33% trimethylamine-ethanol solution was sealed in a screw-topped culture tube and was heated to 80° C. for 24 hr. The mixture was cooled and the solvent evaporated, and the residue recrystallized from isopropanol/ethyl acetate to provide the title compound as a hydrate, a white powder, mp 224°–225° C. (dec). $^1$H NMR (CDCl$_3$) δ 7.43 (d, J=8.7 Hz, 2H) 7.15–7.35 (m, 15H), 6.71 (d, J=8.7 Hz, 2H), 4.82 (s, 2H), 3.73 (t, J=7.7 Hz, 2H), 3.31 (s, 9H), 3.13 (t, J=7.7 Hz, 2H). Anal. calcd. for C$_{31}$H$_{34}$NO.Cl.1.5H$_2$O: C, 74.60; H, 7.47; N, 2.81; Cl, 7.10. Found: C, 74.99; H, 7.49; N, 2.83; Cl, 7.07.

EXAMPLE 34

2-[3-(3,3,3-Triphenylpropoxy)phenyl]acetic acid.

By the method of example 12, methyl 2-(3-hydroxyphenyl)acetate was converted to the title compound. Light yellow solid, 46°–49° C. (triturated with hexanes). $^1$H NMR (CDCl$_3$) δ 7.13–7.34 (m, 16H), 6.81 (d, J=7.4 Hz, 1H), 6.60 (m, 2H), 3.73 (t, J=7.7 Hz, 2H), 3.56 (s, 2H), 3.12 (t, J=7.7 Hz, 2H). IR 2800–3210 (br), 1710 cm$^{-1}$. MS 423 (MH+), 243. Anal. calcd. for C$_{29}$H$_{26}$O$_3$: C, 82.44; H, 6.20. Found: C, 82.34; H, 6.43.

EXAMPLE 35

3-[3-(3,3,3-Triphenylpropoxy)phenyl]propionic acid.

By the method of example 12, methyl 3-(3-hydroxyphenyl)propionate was converted to the title compound, an amorphous solid, in 90% yield. $^1$H NMR (CDCl$_3$) δ 7.09–7.35 (m, 16H), 6.74 (d, J=7.0 Hz, 1H), 6.50–6.55 (m, 2H), 3.73 (t, J=7.6 Hz, 2H), 3.13 (t, J=7.6 Hz, 2H), 2.88 (t, J=7.6 Hz, 2H), 2.63 (t, J=7.6 Hz, 2H). IR 2800–3200 (br), 1708 cm$^{-1}$. MS 437 (MH+). Anal. calcd. for C$_{30}$H$_{28}$O$_3$.0.25 H$_2$O: C, 81.70; H, 6.51. Found: C, 81.92; H, 6.63.

EXAMPLE 36

2-(3,3,3-Triphenylpropoxy)phenylacetic acid.

By the method of example 12, methyl 2-hydroxyphenylacetate was converted into the title compound. White solid, mp=79°–80° C. (MeOH/$H_2O$), 61% yield. $^1H$ NMR (CDCl$_3$) δ 7.11–7.32 (m, 17H), 6.84 (t, J=7.4 Hz, 1H), 6.50 (d, J=8.1 Hz, 1H), 3.74 (t, J=7.6 Hz, 2H), 3.62 (s, 2H), 3.11 (t, J=7.6 Hz, 2H). IR 3350–3450 (br), 1705 cm$^{-1}$. MS 423 (MH+). Anal. calcd. for $C_{29}H_{26}O_3 \cdot 0.4H_2O$: C, 81.05; H, 6.29. Found: C, 81.08; H, 6.28.

EXAMPLE 37

2-[4-(3,3,3-Triphenylpropoxy)phenyl]glycolic acid.

To 3,3,3-triphenylpropanol (6.21 g; 21.53 mmol), p-hydroxybenzaldehyde (3.43 g; 28.08 mmol) and triphenylphosphine (6.88 g; 26.23 mmol) in dry THF (75 mL) under a nitrogen atmosphere at room temperature, was added dropwise over a 30 minute period DEAD (4.2 mL; 26.67 mmol) in dry THF (50 mL). The reaction was heated at reflux for two days. After cooling, the solvent was evaporated in vacuo and the residue chromatographed on a silica column using 5% EtOAc/hexanes. The aldehyde (5.40 g; 64% yield) was isolated as white crystals. mp=129°–130'C. $^1H$ NMR δ 9.83 (s, 1H), 7.74 (d, J=8.7 Hz, 2H), 7.19–7.34 (m, 15H), 6.76 (d, J=8.7 Hz, 2H), 3.82 (t, J=7.7 Hz, 2H), 3.16 (t, J=7.7 Hz, 2H). IR 3030, 1689, 1594 cm$^{-1}$. MS 393 (MH+), 243. Anal. calcd. for $C_{28}H_{24}O_2$: C, 85.68; H, 6.16. Found: C, 85.30; H, 6.22. To this aldehyde (587 mg, 1.50 mmol), lithium chloride (156 mg; 3.68 mmol), and potassium hydroxide (395 mg; 7.04 mmol) in water (2 mL) and 1,4-dioxane (2 mL), was added tribromomethane (0.16 mL; 1.83 mmol). The reaction was heated in an oil bath at 50° C. overnight. The crude reaction was acidified to pH=1 with HCl (1N) and extracted with EtOAc (3×50 mL). The combined organic layers were washed with water (2×50 mL), dried (MgSO$_4$), filtered and evaporated to leave a viscous oil. The crude acid was added to a solution of acetyl chloride (0.15 mL) in methanol (3 mL). After stirring overnight at room temperature under a nitrogen atmosphere, the methanol was evaporated. The residue was dissolved in ether (75 mL), washed with aqueous saturated NaHCO$_3$ (2×50 mL), dried (MgSO$_4$), filtered and evaporated. The methyl ester of the title compound (395 mg; 58% yield from the aldehyde) was obtained as a white solid after recrystallization from ether/hexanes, mp 113°–114.5'C. $^1H$ NMR δ 7.18–7.34 (m, 17H), 6.68 (d, J=8.7 Hz, 2H), 5.07 (d, J=5.4 Hz, 1H), 3.69–3.74 (m, 5H with 3H singlet at δ 3.73), 3.30 (br d, J=5.4 Hz, 1 H, exchangeable), 3.12 (t, J=7.7 Hz, 2H). IR 3485, 2959, 1730, 1508 cm$^{-1}$. MS 453 (MH+), 165 (base). Anal. calcd. for $C_{30}H_{28}O_4$: C, 79.62; H, 6.24. Found: C, 79.43; H, 6.25. This was hydrolyzed by the method of example 12 to yield the title compound as a white foam, mp 55°–58° C. (ether/hexanes), 82% yield. $^1H$ NMR δ 7.20–7.33 (m, 17H), 6.69 (d, J=8.7 Hz, 2H), 5.14 (s, 1H), 3.72 (t, J=7.7 Hz, 2H), 3.12 (t, J=7.7 Hz, 2H). IR 2900–3500 (br), 1719, 1609, 1510 cm$^{-1}$. MS 439 (MH+), 421 (MH+– $H_2O$). Anal. calcd. for $C_{29}H_{26}O_4 \cdot 0.75H_2O$: C, 77.06; H, 6.13. Found: C, 77.34; H, 6.12.

EXAMPLE 38

3-[2-(3,3,3-Triphenylpropoxy)phenyl]propionic acid.

By the method of example 12, methyl 3-(2-hydroxyphenyl)propionate was converted to the title compound. White solid, mp=118°–120° C. (i-PrOH). $^1H$ NMR δ 7.11–7.35 (m, 16H), 7.06 (t, J-7.8 Hz, 1H), 6.82 (t, J=7.0 Hz, 1H), 6.48 (d, J=8.0 Hz, 1H), 3.75 (t, J=7.7 Hz, 2H), 3.15 (t, J=7.7 Hz, 2H), 2.95 (t, J=7.7 Hz, 2H), 2.68 (t, J=7.7 Hz, 2H). IR 2700–3250 (br), 1705 cm$^{-1}$. MS 437 (MH+), 243. Anal. calcd. for $C_{30}H_{28}O_3$: C, 82.54; H, 6.46. Found: C, 82.35; H, 6.46.

EXAMPLE 39

5-[4-(3,3,3-Triphenylpropoxy)phenyl]-1H-tetrazole.

By the method of example 27, 4-hydroxybenzonitrile was converted into the title compound. White solid, mp=232°–233° C. (triturated with dichloromethane). $^1H$ NMR (DMSO-d$_6$) δ 7.92 (d, J=8.7 Hz, 2H), 7.20–7.36 (m, 15H), 6.89 (d, J=8.7 Hz, 2H), 3.79 (t, J=7.1 Hz, 2H), 3.14 (t, J=7.1 Hz, 2H). IR 3260–3650 (br), 1 61 6, 1506 cm$^{-1}$. MS 433 (MH+), 243. Anal. calcd. for $C_{28}H_{24}N_4O \cdot 0.25H_2O$: C, 76.95; H, 5.65; N, 12.82. Found: C, 77.05; H, 5.54; N, 12.68.

EXAMPLE 40

3-[4-(3,3,3-Triphenylpropylthio)phenyl]propylamine.

By the method of example 5, N-(t-butoxycarbonyl)-3-(4-mercapto-phenyl)propylamine was converted to the title compound, obtained as the hydrochloride salt, a tan solid, mp=73°–75° C. Anal. calcd. for $C_{30}H_{31}NS \cdot HCl \cdot 0.5H_2O$: C, 74.58; H, 6.88; N, 2.90. Found: C, 74.61; H, 7.02; N, 2.80.

EXAMPLE 41

5-[4-(3,3,3-Triphenylpropoxy)phenyl]thiazolidine-2,4-dione.

The intermediate hydroxy ester was prepared by the method stated in example 37. To the hydroxy ester (225 mg; 0.497 mmol) in benzene (3 mL), was added thionyl chloride (48 μl; 0.66 mmol) and pyridine (48μΛ; 0.59 mmol) under a nitrogen atmosphere. After stirring overnight at room temperature, the benzene was evaporated. The residue was dissolved in EtOAc (75 mL) and washed with water (2×30 mL), dried (MgSO$_4$), filtered and evaporated. Chromatography on silica gel with 10% EtOAc/hexanes afforded chloroester as a viscous oil (210 mg; 90% yield). $^1H$ NMR δ 7.18–7.34 (m, 17H), 6.68 (d, J=8.8 Hz, 2H), 5.29 (s, 1H), 3.71–3.76 (m, 5H with 3H singlet at a 3.74), 3.13 (t, J=7.7 Hz, 2H). Chloroester (210 mg; 0.4461 mmol) and thiourea (71.2 mg; 0.9353 mmol) in sulfolane (2 mL) were heated in an oil bath at 110° C. for 4.5 h under a nitrogen atmosphere. The reaction was cooled slightly and aqueous HCl (1N; 2.0 mL) was carefully added. The reaction was heated to 100° C. overnight, poured into water (50 mL) and extracted with ether (3×50 mL). The organic layers were washed with water (4×25 mL), dried (MgSO$_4$), filtered and evaporated. The crude product was chromatographed on a silica gel column using 25% EtOAc/hexanes to give title compound (202 mg; 58% yield) as a white foam. mp=85°–87° C. $^1H$ NMR δ 8.02 (br s, 1H), 7.22–7.31 (m, 17H), 6.70 (d, J=8.6 Hz, 2H), 5.30 (s, 1H), 3.73 (t, J=7.6 Hz, 2H), 3.13 (t, J=7.6 Hz, 2H). IR 2950–3200 (br), 1757, 1700, 1510 cm$^{-1}$. MS 480 (MH+). Anal. calcd. for $C_{30}H_{25}NO_3S \cdot 0.25H_2O$: C, 74.73; H, 5.31; N, 2.89. Found: C, 74.44; H, 5.56; N, 2.73.

EXAMPLE 42

2-Hydroxy-6-(3,3,3-triphenylpropoxy)benzoic acid.

By the method of example 12, methyl 2,6-dihydroxybenzoate was converted into the methyl ester of the title compound, isolated by chromatography on silica gel with a gradient of dichloromethane in hexane. This was saponified to give the title compound, isolated as a hydrate, a white solid, mp 167°–168° C. after recrystallization from ether-hexanes. $^1$H NMR (CDCl$_3$) δ 12.13 (s, 1H), 11.38 (s, 1H), 7.21–7.34 (m, 16H), 6.65 (d, J=9 Hz, 1H), 6.10 (d, J=9 Hz, 1H), 4.05 (dd, J=7.9 and 7.3 Hz, 2H), 3.20 (dd, J=7.9 and 7.3 Hz, 2H). MS m/z 425 (MH+). Anal. calcd. for C$_{28}$H$_{24}$O$_4$.0.25H$_2$O: C, 78.39; H, 5.76. Found: C, 78.42; H, 5.74.

EXAMPLE 43 trans 3-(3,3,3-Triphenylpropoxy)cinnamic acid.

By the method of example 12, methyl 3-hydroxycinnamate was converted to the title compound, obtained as a hydrate, a white solid, mp=104°–109° C. (water), 98% yield. $^1$H NMR (DMSO-d$_6$) δ 7.16–7.36 (m, 17H), 7.03–7.09 (m, 1H), 6.85 (br s, 1H), 6.62 (d, J=7.8 Hz, 1H), 6.40 (d, J=15.9 Hz, 1H), 3.71 (t, J=7.2 Hz, 2H), 3.09 (t, J=7.2 Hz, 2H). IR 3200–3400 (br), 1639, 1578 cm$^{-1}$. MS 435 (MH+), 417 (M–OH)+, 243 (base). Anal. calcd. for C$_{30}$H$_{26}$O$_3$.1.25 H$_2$O: C, 78.84; H, 6.29. Found: C, 78.75; H, 5.96.

EXAMPLE 44

3-(3,3,3-triphenylpropoxy)phenoxyacetic acid.

To 3,3,3-triphenylpropanol (2.00 g, 6.93 mmol), triphenylphosphine (6.93 mmol), and 3-(benzenesulfonyloxy) phenol (1.74 g, 6.93 mmol) in benzene (10 mL), was added DEAD (6.93 mmol) in benzene (10 mL). The reaction was heated at 60° C. for 16 hours. After cooling, the volatiles were evaporated and the residue chromatographed on a silica gel column using 1:1 dichloromethane/hexanes. Recrystallization from ether afforded 3-(3,3,3-triphenylpropoxy)phenyl benzenesulfonate as a white solid, mp=124°–125° C., in 75% yield. $^1$H NMR (CDCl$_3$) δ 7.77–7.80 (m, 2H), 7.41–7.56 (m, 2H), 7.18–7.32 (m, 16H), 7.08 (t, J=8.2 Hz, 1H), 6.51–6.59 (m, 2H), 6.21 (t, J=2.3 Hz, 1H), 3.55 (t, J=7.7 Hz, 2H), 3.05 (t, J=7.7 Hz, 2H). IR 3056, 1612, 1582, 1491 cm$^{-1}$. MS 538 (M+NH$_4$)+, 521 (MH+), 243. Anal. calcd. for C$_{33}$H$_{28}$O$_4$S: C, 76.13; H, 5.42. Found: C, 75.58; H, 5.50. Potassium hydroxide (4.69 g, 0.084 mol) in water (6 mL) and methanol (30 mL) was added to this material (17.4 g, 0.033 mol) in methanol (80 mL). The reaction was heated at 50° C. for 20 hours, cooled, and poured into water (150 mL), and acidified to pH=1 with concentrated HCl. This was extracted with several portions of ether. The combined ethereal layers were washed with water, dried, filtered and evaporated to afford 3-(3,3,3-triphenylpropoxy)phenol as a white amorphous solid, in 96% yield. $^1$H NMR (CDCl$_3$) δ 7.10–7.33 (m, 15H), 7.04 (t, J=8.1 Hz, 1H), 6.34 (dt, J=8.0, 1.0 Hz, 1H), 6.29 (dd, J=2.1, 8.5 Hz, 1H), 6.16 (t, J=2.3 Hz, 1H), 4.65 (s, 1H), 3.67–3.74 (m, 2H), 3.12 (t, J=7.8 Hz, 2H). IR 3200–3500 (br), 1595, 1492 cm$^{-1}$. MS (FAB) 381 (MH+), 243. Anal. calcd. for C$_{27}$H$_{24}$O$_2$.0.25H$_2$O: C, 84.23; H, 6.41. Found: C, 84.26; H, 6.66. To the above phenol (2.59 mmol) in acetone (15 mL), was added potassium carbonate (5.18 mmol) and methyl bromoacetate (2.75 mmol). The reaction was heated at reflux overnight. After cooling, the reaction was filtered through a pad of Celite. The resulting flitrate was evaporated and the residue dissolved in methylene chloride. This was washed with water, dried (MgSO$_4$), filtered and evaporated to afford methyl 3-(3,3,3-triphenylpropoxy)phenoxyacetate. White solid, mp=103°–105° C. (ether), 85%yield. $^1$H NMR (CDCl$_3$) δ 7.17–7.33 (m, 15H), 7.09 (t, J=8.2 Hz, 1H), 6.29–6.43 (m, 3H), 4.57 (s, 2H), 3.79 (s, 3H), 3.70 (t, J=7.7 Hz, 2H), 3.12 (t, J=7.7 Hz, 2H). IR 1768, 1602, 1152 cm$^{-1}$. MS 453 (MH+), 243. Anal. calcd. for C$_{30}$H$_{28}$O$_4$.0.2H$_2$O: C, 78.99; H, 6.28. Found: C, 79.04; H, 6.18. The hydrolysis of the ester to the acid was performed as described in example 12, providing the title compound as a white solid, mp 69°–71 ° C., in 89% yield. $^1$H NMR (CDCl$_3$) δ 7.15–7.30 (m, 15H), 6.95 (t, J=8.2 Hz, 1H), 6.25–6.35 (m, 3H), 4.40 (s, 2H), 3.74 (t, J=7.7 Hz, 2H), 3.05 (t, J=7.7 Hz, 2H). IR 3000–3200 (br), 1719, 1595 cm$^{-1}$. MS 439 (MH+), 243. Anal. calcd. for C$_{29}$H$_{26}$O$_4$.0.7H$_2$O: C, 77.21; H, 6.12. Found: C, 77.04; H, 5.88.

EXAMPLE 45

2-(3,3,3-triphenylpropoxy)phenoxyacetic acid

By the method of example 44, 2-(benzenesulfonyloxy) phenol was converted to the title compound, a white solid, mp 137°–139° C. (ether), in 62% yield. $^1$H NMR (DMSO-d$_6$) δ 7.22–7.38 (m, 15H), 6.66–6.79 (m, 3H), 6.51 (d, J=8.0 Hz, 1H), 3.62 (t, J=7.6 Hz, 2H), 3.15 (t, J=7.6 Hz, 2H). IR 3200–3500 (br), 1625, 1503 cm$^{-1}$. MS 456 (M+NH4)+, 271,243.

EXAMPLE 46

4-[3-(3,3,3-triphenylpropoxy)phenoxy]butyric acid.

By the method of example 44, ethyl 4-bromobutyrate was converted to the title compound, a white solid, mp 53°–55° C., in 88% yield. $^1$H NMR (CDCl$_3$) δ 7.12–7.29 (m, 15H), 6.96 (t, J=8.2 Hz, 1H), 6.34 (d, J=8.2 Hz, 1H), 6.18–6.23 (m, 2H), 3.90–4.20 (br s ,1H), 3.78–3.82 (m, 2H), 3.66 (t, J=7.6 Hz, 2H), 3.07 (t, J=7.6 Hz, 2H), 2.36–2.42 (m, 5H). IR 3300–3550 (br), 1708, 1593 cm$^{-1}$. MS 467 (MH+), 243. Anal. calcd. for C$_{31}$H$_{30}$O$_4$.1.0H$_2$O: C, 76.84; H, 6.66. Found: C, 76.85; H, 6.55.

EXAMPLE 47

4-[2-(3,3,3-triphenylpropoxy)phenoxy]butyric acid.

By the method of example 44, ethyl 4-bromobutyrate was converted to the title compound, a white solid, mp 107°–108° C., in 83% yield. $^1$H NMR (CDCl$_3$) δ 7.16–7.34 (m, 15H), 6.78–6.86 (m, 3H), 6.57 (d, J=7.1 Hz, 1H), 4.06 (t, J=6.1 Hz ,2H), 3.76 (t, J=7.9 Hz, 2H), 3.18 (t, J=7.9 Hz, 2H), 2.63 (t, J=7.1 Hz, 2H), 2.05–2.17 (m, 2H). IR 2900–3200 (br), 1718, 1507 cm$^{-1}$. MS 467 (MH+), 271, 243. Anal. calcd. for C$_{31}$H$_{30}$O$_4$.0.6H$_2$O: C, 78.00; H, 6.59. Found: C, 77.68; H, 6.96.

EXAMPLE 48

4-(3,3,3-triphenylpropoxy)phenoxyacetic acid.

4-(3,3,3-Triphenylpropoxy)benzaldehyde (2.16 g, 5.5 mmol), and mCPBA (2.85g, 8.25 mmol) in methylene chloride (60 mL) were heated at reflux under a nitrogen atmosphere for 4 h. After cooling, the volatiles were evaporated and the residue dissolved in ether (250 mL). This was washed with saturated NaHCO$_3$ (2×150 mL), brine (150 mL), dried (MgSO$_4$), filtered and evaporated to afford the crude formate. $^1$H NMR (CDCl$_3$) δ 8.25 (s, 1H), 7.20–7.34 (m, 15H), 6.95 (d, J=9.0 Hz, 2H), 6.68 (d, J=9.0 Hz, 2H), 3.71 (t, J=7.7 Hz, 2H), 3.13 (t, J=7.7 Hz, 2H). Attempts to purify the formate (florisil chromatography) lead to 4-(3,3, 3-triphenylpropoxy)phenol which was isolated as an amorphous solid (57% yield from the aldehyde). $^1$H NMR (CDCl$_3$) δ 7.16–7.33 (m, 15H), 6.67 (d, J=9.0 Hz, 2H), 6.58 (d, J=9.0 Hz, 2H), 4.35 (s, 1H), 3.63–3.68 (m, 2H), 3.10 (t, J=7.8 Hz, 2H). By the method of example 44, methyl bromoacetate was converted into the title compound, a white solid, mp 66°–68° C. $^1$H NMR (CDCl$_3$) δ 7.16–7.32 (m, 15H), 6.76 (d, J=9.1 Hz, 2H), 6.62 (d, J=9.1 Hz, 2H), 4.53 (s, 2H), 3.66 (t, J=7.9 Hz, 2H), 3.10 (t, J=7.9 Hz, 2H). Anal. calcd. for $C_{29}H_{26}O_4 \cdot 0.5H_2O$: C, 77.83; H, 6.08. Found: C, 77.79; H, 6.04.

EXAMPLE 49

4-[4-(3,3,3-triphenylpropoxy)phenoxyl]butyric acid.

By the method of example 48, ethyl 4-bromobutyrate was converted to the title compound, mp=138°–139° C.

We claim:

1. A method of treating bacterial infections in mammals by administering to a mammal suffering from such infection a therapeutically effective amount of a compound selected from those of the formula 1:

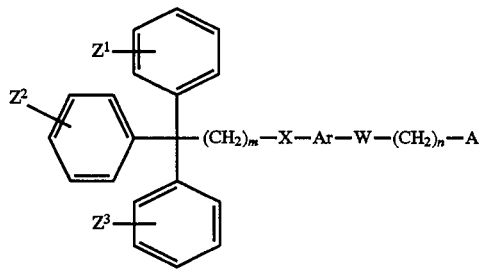

wherein $Z^1$, $Z^2$, and $Z^3$ are independently H, halogen, $C_1$–$C_6$ alkyl, $C_1$–$C_6$ alkoxy, hydroxy, amino, or nitro;

m is an integer from 1–5;

X is $CH_2O$, $CH_2S$, $CH_2NR$, $C(O)NR$, $CH_2OC(O)CH_2$, or $CH_2OC(O)CH_2CH_2$;

Ar is aryl optionally substituted with one to three substituents selected from halogen, hydroxy, $C_1$–$C_6$ alkyl and $C_1$–$C_6$ alkoxy;

W is oxygen, sulfur, or a bond;

n is an integer from 0–5;

A is selected from:
(a) $NR^1R^2$;
(b) $N^+R^1R^2R^3$ $B^-$; and
(c) guanidino;

wherein:

R, $R^1$, $R^2$, and $R^3$ are independently H, C1–C6 lower alkyl, or aryl$C_1$–$C_6$ alkyl;

$B^-$ is a pharmaceutically acceptable counterion; and aryl is phenyl, biphenyl or naphthyl;

with the provisos that:
where n is 0, A is not $NH_2$; and
where n is 0 or 1, W is a bond;

and the pharmaceutically acceptable salts and prodrug forms thereof.

2. A method according to claim 1 wherein X is selected from $CH_2O$ and $CH_2S$.

3. A method according to claim 1 wherein Ar is selected from 1,2-phenylene, 1,3-phenylene, 1,4-phenylene, 1,6-naphthylene, 6,1-naphthylene, 1,5-naphthylene, 2,5-naphthylene, 5,2-naphthylene, and 2,6-naphthylene.

4. A method according to claim 1 wherein:

X is selected from $CH_2O$, and $CH_2S$;

Ar is selected from 1,2-phenylene, 1,3-phenylene, 1,4-phenylene, 1,6-naphthylene, 6,1-naphthylene, 1,5-naphthylene, 2,5-naphthylene, 5,2-naphthylene, and 2,6-naphthylene;

where Ar may optionally be further substituted with one to three substituents selected from halogen, $C_1$–$C_6$ alkyl, hydroxy, and $C_1$–$C_6$ alkoxy;

n is 0, 1, 2, or 3;

m is 1;

W is a bond;

and A is selected from guanidino, $NR^1R^2$, and $N^+R^1R^2R^3$ $B^-$; wherein $R^1$, $R^2$, and $R^3$ are independently selected from H, $C_1$–$C_6$lower alkyl and aryl$C_1$–$C_6$alkyl;

$B^-$ is a pharmaceutically acceptable counterion; and aryl is phenyl, biphenyl or naphthyl;

with the proviso that:
where n is 0, A is not $NH_2$;

and the pharmaceutically acceptable salts and prodrug forms thereof.

5. A compound selected from those of the formula 1:

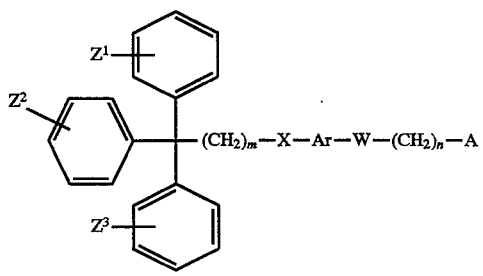

wherein $Z^1$, $Z^2$, and $Z^3$ are independently H, halogen, $C_1$–$C_6$ alkyl, $C_1$–$C_6$ alkoxy, hydroxy, amino, or nitro;

m is an integer from 1–5;

X is $CH_2O$, $CH_2S$, $CH_2NR$, $C(O)NR$, $CH_2OC(O)CH_2$, or $CH_2OC(O)CH_2CH_2$;

Ar is aryl optionally substituted with one to three substituents selected from halogen, hydroxy, $C_1$–$C_6$ alkyl and $C_1$–$C_6$ alkoxy;

W is oxygen, sulfur, or a bond;

n is an integer from 0–5;

A is selected from:
(a) $NR^1R^2$;
(b) $N^+R^1R^2R^3$ $B^-$; and
(c) guanidino;

wherein:

R, $R^1$, $R^2$, and $R^3$ are independently H, $C_1$–$C_6$ lower alkyl, or aryl$C_1$–$C_6$ alkyl;

$B^-$ is a pharmaceutically acceptable counterion; and aryl is phenyl, biphenyl or naphthyl;

with the provisos that:
where n is 0, A is not $NH_2$; and
where n is 0 or 1, W is a bond;

and the pharmaceutically acceptable salts and prodrug forms thereof.

6. A compound according to claim 5 wherein X is selected from $CH_2O$ and $CH_2S$.

7. A compound according to claim 5 wherein Ar is selected from 1,2-phenylene, 1,3-phenylene, 1,4-phenylene, 1,6-naphthylene, 6,1-naphthylene, 1,5-naphthylene, 2,5-naphthylene, 5,2-naphthylene, and 2,6-naphthylene.

8. A compound according to claim 1 wherein:

X is selected from $CH_2O$, and $CH_2S$;

Ar is selected from 1,2-phenylene, 1,3-phenylene, 1,4-phenylene, 1,6-naphthylene, 6,1-naphthylene, 1,5-naphthylene, 2,5-naphthylene, 5,2-naphthylene, and 2,6-naphthylene;

where Ar may optionally be further substituted with one to three substituents selected from halogen, $C_1$–$C_6$ alkyl, hydroxy, and $C_1$–$C_6$ alkoxy;

n is 0, 1, 2, or 3;

m is 1;

W is a bond;

and A is selected from guanidino, $NR^1R^2$, and $N^+R^1R^2R^3$ $B^-$;

wherein $R^1$, $R^2$, and $R^3$ are independently selected from H, $C_1$–$C_6$ lower alkyl and aryl$C_1$–$C_6$alkyl;

$B^-$ is a pharmaceutically acceptable counterion; and aryl is phenyl, biphenyl or naphthyl;

with the proviso that:

where n is 0, A is not $NH_2$;

and the pharmaceutically acceptable salts and prodrug forms thereof.

9. A pharmaceutical composition for treating bacterial infections comprising an effective amount of a compound selected from claim 5 in association with a pharmaceutically acceptable carrier.

10. The compound according to claim 5, N-(2-(4-(3,3,3-triphenylpropoxy) phenyl)ethylguanidine.

11. The compound according to claim 5, 3-[4-(3,3,3-Triphenylpropylthio)phenyl]propylamine.

12. The compound according to claim 5, 2-(4-(3,3,3-triphenylpropoxy)phenyl)ethylamine.

13. The compound according to claim 5, N-(2-(4-(5,5,5-triphenylpentoxy)phenyl)ethylguanidine.

14. The compound according to claim 5, 4-(3,3,3-triphenylpropoxy)benzylamine.

15. The compound according to claim 5, 6-(3,3,3-Triphenylpropoxy)-2-naphthylmethylamine.

16. The compound according to claim 5, N-(2-(4-(3,3,3-triphenylbutoxy)phenyl)ethylguanidine.

* * * * *